US009956279B2

(12) United States Patent
Ma et al.

(10) Patent No.: US 9,956,279 B2
(45) Date of Patent: May 1, 2018

(54) VACCINE FOR PCV2 AND MYCOPLASMA

(71) Applicant: Protatek International, Inc., St. Paul, MN (US)

(72) Inventors: Shi Jun Ma, Shoreview, MN (US); Jing Sui, Blaine, MN (US)

(73) Assignee: Protatek International, Inc., St. Paul, MN (US)

( * ) Notice: Subject to any disclaimer, the term of this patent is extended or adjusted under 35 U.S.C. 154(b) by 0 days. days.

(21) Appl. No.: 15/483,597

(22) Filed: Apr. 10, 2017

(65) Prior Publication Data

US 2017/0216424 A1  Aug. 3, 2017

Related U.S. Application Data

(63) Continuation of application No. 14/889,044, filed as application No. PCT/US2014/037246 on May 8, 2014, now Pat. No. 9,649,370.

(60) Provisional application No. 61/821,011, filed on May 8, 2013.

(51) Int. Cl.
*A61K 39/02* (2006.01)
*C12N 7/00* (2006.01)
*A61K 39/12* (2006.01)
*A61K 47/24* (2006.01)
*A61K 39/00* (2006.01)

(52) U.S. Cl.
CPC .......... *A61K 39/12* (2013.01); *A61K 39/0241* (2013.01); *A61K 47/24* (2013.01); *C12N 7/00* (2013.01); *A61K 2039/521* (2013.01); *A61K 2039/5252* (2013.01); *A61K 2039/543* (2013.01); *A61K 2039/545* (2013.01); *A61K 2039/552* (2013.01); *A61K 2039/55505* (2013.01); *A61K 2039/55566* (2013.01); *A61K 2039/55577* (2013.01); *A61K 2039/575* (2013.01); *A61K 2039/70* (2013.01); *C12N 2750/10021* (2013.01); *C12N 2750/10034* (2013.01); *C12N 2750/10071* (2013.01)

(58) Field of Classification Search
None
See application file for complete search history.

(56) References Cited

U.S. PATENT DOCUMENTS

| | | | |
|---|---|---|---|
| 5,733,555 A | 3/1998 | Chu | |
| 6,217,883 B1 | 4/2001 | Allan et al. | |
| 6,224,882 B1 | 5/2001 | Smith et al. | |
| 6,368,601 B1 | 4/2002 | Allan et al. | |
| 6,497,883 B1 | 12/2002 | Bublot et al. | |
| 6,943,152 B1 | 9/2005 | Audonnet et al. | |
| 6,953,581 B2 | 10/2005 | Allan et al. | |
| 7,018,638 B2 | 3/2006 | Chu et al. | |
| 7,109,025 B1 | 9/2006 | Eloit et al. | |
| 7,122,192 B2 | 10/2006 | Allan et al. | |
| 7,169,394 B2 | 1/2007 | Chu et al. | |
| 7,223,594 B2 | 5/2007 | Jestin et al. | |
| 7,358,075 B2 | 4/2008 | Allibert et al. | |
| 7,371,395 B2 | 5/2008 | Parisot et al. | |
| 7,476,507 B2 | 1/2009 | Allibert et al. | |
| 7,608,279 B2 | 10/2009 | Parisot et al. | |
| 7,622,124 B2 | 11/2009 | Chu et al. | |
| 7,691,368 B2 | 4/2010 | Parisot et al. | |
| 7,740,866 B2 | 6/2010 | Jestin et al. | |
| 7,758,865 B2 | 7/2010 | Jestin et al. | |
| 7,943,298 B2 | 5/2011 | Fachinger et al. | |
| 7,951,907 B2 | 5/2011 | Jestin et al. | |
| 8,008,001 B2 | 8/2011 | Roerink et al. | |
| 8,119,143 B2 | 2/2012 | Roof et al. | |
| 8,124,723 B2 | 2/2012 | Jestin et al. | |
| 8,496,940 B2 | 7/2013 | Fachinger et al. | |
| 8,715,690 B2 | 5/2014 | Jestin et al. | |
| 8,865,183 B2 | 10/2014 | Fachinger et al. | |
| 9,056,909 B2 | 6/2015 | Chu et al. | |
| 9,101,561 B2 | 8/2015 | Roof et al. | |
| 9,101,571 B2 | 8/2015 | Kuo et al. | |
| 9,120,859 B2 | 9/2015 | Galvin et al. | |
| 9,125,885 B2 | 9/2015 | Nitzel et al. | |
| 9,125,886 B2 | 9/2015 | Nitzel et al. | |
| 9,132,187 B2 | 9/2015 | Fachinger et al. | |
| 9,561,270 B2 | 2/2017 | Kohler et al. | |
| 9,649,369 B2 | 5/2017 | Nitzel et al. | |
| 9,649,370 B2* | 5/2017 | Ma | A61K 39/0241 |
| 9,650,601 B2 | 5/2017 | Nitzel et al. | |
| 9,657,063 B2 | 5/2017 | Kuo et al. | |
| 2003/0092897 A1 | 5/2003 | Walker et al. | |
| 2009/0092636 A1 | 4/2009 | Roof et al. | |

(Continued)

FOREIGN PATENT DOCUMENTS

WO    95/17210    6/1995
WO    99/18214    4/1999

(Continued)

OTHER PUBLICATIONS

Hitchman et al.: "Baculovirus Expression Systems for Recombinant Protein Production in Insect Cells"; ResearchGate, Recent Patents on Biotechnology, 2009, 3, pp. 46-54.
Sun et al.: "Advances in saponin-based adjuvants"; Elsevier, Vaccine 27, 2009, pp. 1787-1796.
Pointon et al.: "Disease surveillance at slaughter" 1999, In: Straw, B.E., D'Allaire, S., Mengeling, W.L., Taylor, D.J. (Eds.): "Diseases of Swine, 8th Ed.", Iowa State University Press, Ames, Iowa, USA, pp. 1111-1132.
Product Information: "Circumvent® PCV M, Porcine Circovirus Vaccine, Type 2, Killed Baculovirus Vector, Mycoplasma Hyopneumoniae Bacterin", 2011, Intervet/Schering-Plough Animal Health, NJ, USA (2 pages).
Label: "Porcine Circovirus Vaccine, Type 2, Killed Baculovirus Vector, Mycoplasma Hyopneumoniae Bacterin" Circumvent® PCV M 250 doses 500 mL Code 046494, 2011, Intervet Inc., NE, USA (1 page).

(Continued)

Primary Examiner — Padmavathi Baskar
(74) Attorney, Agent, or Firm — Merchant & Gould P.C.

(57) ABSTRACT

A premixed multivalent vaccine in ready-to-use form comprising PCV2 ORF2 capsid antigen and *M. hyopneumoniae* antigen that reduces or prevents PCV2 infection and/or *M. hyopneumoniae* infection in pigs after a single dose administration of the vaccine is disclosed.

16 Claims, 10 Drawing Sheets

(56) References Cited

U.S. PATENT DOCUMENTS

| | | |
|---|---|---|
| 2009/0317423 A1 | 12/2009 | Roof et al. |
| 2010/0062018 A1 | 3/2010 | Chu et al. |
| 2011/0129494 A1 | 6/2011 | Detraz et al. |
| 2011/0305725 A1 | 12/2011 | Wu |
| 2015/0297707 A1 | 10/2015 | Roof et al. |
| 2015/0306200 A1 | 10/2015 | Gonzalez Gonzalez et al. |
| 2016/0220658 A1 | 8/2016 | Nitzel et al. |
| 2016/0346372 A1 | 12/2016 | Shao et al. |

FOREIGN PATENT DOCUMENTS

| | | |
|---|---|---|
| WO | 03/005952 | 1/2003 |
| WO | 2016091998 | 6/2016 |

OTHER PUBLICATIONS

Label: "Porcine Circovirus Vaccine, Type 2, Killed Baculovirus Vector, Mycoplasma Hyopneumoniae Bacterin" Circumvent® PCV M 50 doses 100 mL Code 029726, 2011, Intervet Inc., NE, USA (1 page).

"Maximize Feed Efficiencies, Minimize Production Risk"; Circumvent® PCV M, Merck Animal Health (Intervet Inc.), 2012 (1 page).

International Search Report for PCT/US2014/037246, dated Sep. 25, 2014.

European Search Report for European Application No. 14794866.5, dated Nov. 23, 2016.

Eggen et al., "Combining Mycoplasma Hyopneumoniae and Porcine Circovirus Type 2, a research report," (2011) Proceedings of the 5th Asian Pig Veterinary Society Congress Mar. 2011.

Eggen et al., "One dose Vaccination against Mycoplasma Hyopneumoniae and porcine circovirus type 2," Proceedings of the 21st Asian Pig Veterinary Society Congress Jul. 2010.

Farreres et al., "Serology and safety of the simultaneous use of Porcilis PCV and M+PAC in the field," Proceedings of the 21st Asian Pig Veterinary Society Congress Jul. 2010.

Ruiz et al, "Porcine Circovirus Associated Diseases—Control—Clinical and pathologic lesions after simultaneous vaccination with PCV2 and Mycoplasma vaccine in 3 week old piglets," Proceedings of the 21st Asian Pig Veterinary Society Congress Jul. 2010.

Herbich et al, Field trial on the simultaneous vaccination against porcine circovirus type 2 and Mycoplasma hyopneumoniae, Tierarztl Prax Ausg G Grosstiere Nutztiere (2013).

Rivera et al., "Ginseng and aluminum hydroxide act synergistically as vaccine adjuvants," Vaccine, vol. 21, No. 11-12, (2003).

Sun et al., "Advances in saponin-based adjuvants," Vaccine, vol. 27, No. 12, (2009).

* cited by examiner

SEQUENCE LISTING

```
<160> NUMBER OF SEQ ID NOS: 5

<210> SEQ ID NO 1
<211> LENGTH: 702
<212> TYPE: DNA
<213> ORGANISM: Porcine circovirus type 2b
<220> FEATURE:
<221> NAME/KEY: misc_feature
<222> LOCATION: (1)..(702)
<223> OTHER INFORMATION: ORF2 gene

<400> SEQUENCE: 1
atgacgtatc caaggaggcg ttaccggaga agaagacacc gcccccgcag ccatcttggc      60
cagatcctcc gccgccgccc ctggctcgtc cacccccgcc accgttaccg ctggagaagg     120
aaaaatggca tcttcaacac ccgcctatcc cgcaccttcg gatatactat caagcgaacc     180
acagtcagaa cgccctcctg ggcggtggac atgatgagat tcaatattaa tgactttctt     240
cccccaggag gggctcaaa cccccgctct gtgccctttg aatactacag aataagaaag     300
gttaaggttg aattctggcc ctgctccccg atcacccagg gtgacagggg agtgggctcc     360
agtgctgtta ttctagatga taactttgta acaaaggcca cagccctcac ctatgacccc     420
tatgtaaact actcctcccg ccataccata acccagccct tctcctacca ctcccgctac     480
tttaccccca aacctgtcct agattccact attgattact tccaaccaaa caacaaaaga     540
aaccagctgt ggctgagact acaaactgct ggaaatgtag accacgtagg cctcggcatt     600
gcgttcgaaa acagtataaa cgaccaggaa tacaatatcc gtgtaaccat gtatgtacaa     660
ttcagagaat ttaatcttaa agaccccca cttaaccctt aa                        702

<210> SEQ ID NO 2
<211> LENGTH: 38
<212> TYPE: DNA
<213> ORGANISM: Artificial Sequence
<220> FEATURE:
<223> OTHER INFORMATION: Primer BHPCV2bF

<400> SEQUENCE: 2
atatatggat ccatgacgta tccaaggagg cgttaccg                             38

<210> SEQ ID NO 3
<211> LENGTH: 40
<212> TYPE: DNA
<213> ORGANISM: Artificial Sequence
<220> FEATURE:
<223> OTHER INFORMATION: Primer HDPCV2bR

<400> SEQUENCE: 3
gatcgcaagc ttttaagggt taagtggggg gtctttaaga                           40

<210> SEQ ID NO 4
<211> LENGTH: 38
<212> TYPE: DNA
<213> ORGANISM: Artificial Sequence
<220> FEATURE:
<223> OTHER INFORMATION: Primer XHPCV2bF

<400> SEQUENCE: 4
attatactcg agatgacgta tccaaggagg cgttaccg                             38

<210> SEQ ID NO 5
<211> LENGTH: 40
<212> TYPE: DNA
<213> ORGANISM: Artificial Sequence
```

```
<220> FEATURE:
<223> OTHER INFORMATION: Primer KPPCV2bR

<400> SEQUENCE: 5
gctcacggta ccttaagggt taagtggggg gtctttaaga                              40
```

VACCINE FOR PCV2 AND MYCOPLASMA

CROSS-REFERENCE TO RELATED APPLICATIONS

This application is a continuation of U.S. application Ser. No. 14/889,044, filed Nov. 4, 2015, which is a US National Stage application of PCT/US2014/037246, filed May 8, 2014 which claims priority to U.S. Provisional patent application Ser. No. 61/821,011, filed May 8, 2013, the contents of all of which are hereby incorporated by reference in their entireties.

INTRODUCTION

Diseases associated with porcine circovirus type 2 (PCV2) and *Mycoplasma hyopneumoniae* infection annually cost the swine industry millions in dollars of losses. Post-weaning multisystem wasting syndrome (PWMS) is associated with PCV2 infection of pigs. PWMS is clinically characterized by one or more of wasting, paleness of the skin, respiratory distress, diarrhea, and jaundice. In PWMS, it has been observed that macroscopic and microscopic lesions appear on multiple tissues and organs in infected pigs, with lymphoid organs being a common site for lesions. Mortality rates for pigs infected with PCV2, especially pigs exhibiting wasting, is high and infected pigs are also prone to developing secondary bacterial infections, like Glasser disease, pulmonary pasteruellosis, colibacilosis, and salmonellosis.

*Mycoplasma hyopneumoniae* is a causative agent of porcine enzootic pneumonia, a respiratory disease that is widespread among swine and commonly found in most swine herds. *M. hyopneumoniae* attacks the cilia of epithelial cells in the lungs causing death of the epithelial cells which results in lesions in the lungs of an infected pig. *M. hyopneumoniae* infection causes a significant reduction of the growing weight of pigs and facilitates entry of PRRSV and other respiratory pathogens into the lungs. The economic losses associated with increased mortality and poor growth performance due to PCV2 and *M. hyopneumoniae* infection are therefore of significant concern in the swine industry.

A premixed multivalent vaccine in ready-to-use form comprising PCV2 antigen and *M. hyopneumoniae* antigen that elicits protective immunity against PCV2 infection and *M. hyopneumoniae* infection after a single dose administration of the vaccine would be useful in reducing morbidity and mortality associated with diseases caused by these infectious agents.

SUMMARY

A multivalent single dose vaccine is disclosed. Each dose of the vaccine comprises an immunogenic amount of recombinant PCV2 ORF capsid antigen; an immunogenic amount of *Mycoplasma hyopneumoniae* antigen; a two component adjuvant system; and a physiologically acceptable vehicle. The first component of the adjuvant system comprises a saponin adjuvant and the second component of the adjuvant system comprises an oil-in-water adjuvant or aluminum adjuvant. The *M. hyopneumoniae* antigen can be inactivated or attenuated *M. hyopneumoniae* or a lysate or sonicate of an attenuated, inactivated, or virulent *M. hyopneumoniae*. The vaccine can further include a non-ionic detergent and/or a preservative, such as thimerosal.

In embodiments, a dose of the vaccine comprises about 1 ml to about 2 ml. Each dose of the vaccine elicits an immune response in a pig vaccinated with the vaccine that reduces or prevents one or more of:
 viremia caused by PCV2,
 PCV2 virus colonization of lymphoid tissues,
 lymphoid depletion associated with PCV2,
 clinical signs associated with PCV2 infection, or
 lung lesions caused by *M. hyopneumoniae* infection
compared to a pig that is not vaccinated with the vaccine or administered a negative control before challenge with a field strain of PCV2 or *M. hyopneumoniae*. In an embodiment, administration of a single dose of the vaccine to a pig reduces the severity of or prevents conditions associated with PCV2 infection comprising one or more of wasting, paleness of the skin, respiratory distress, diarrhea, and jaundice.

A method of reducing or preventing PCV2 infection and/or *M. hyopneumoniae* infection in a pig is also disclosed. The method typically comprises administering to the pig a single dose of the vaccine of the disclosure. The vaccine is typically administered to the pig within about 1 to about 2 weeks of birth.

A method of formulating a multivalent single dose vaccine of the disclosure is also disclosed. The method typically comprises solubilizing an immunogenic amount of *M. hyopneumoniae* antigen in a non-ionic detergent; mixing the solubilized *M. hyopneumoniae* antigen with saponin to form a partially adjuvanted mixture; solubilizing an immunogenic amount of recombinant PCV2 ORF2 capsid antigen in a non-ionic detergent; mixing the solubilized capsid antigen with the partially adjuvanted mixture to form a partially adjuvanted vaccine; and mixing the partially adjuvanted vaccine with an oil-in-water adjuvant or aluminum adjuvant to form the multivalent single dose vaccine.

DETAILED DESCRIPTION

Figure 1:
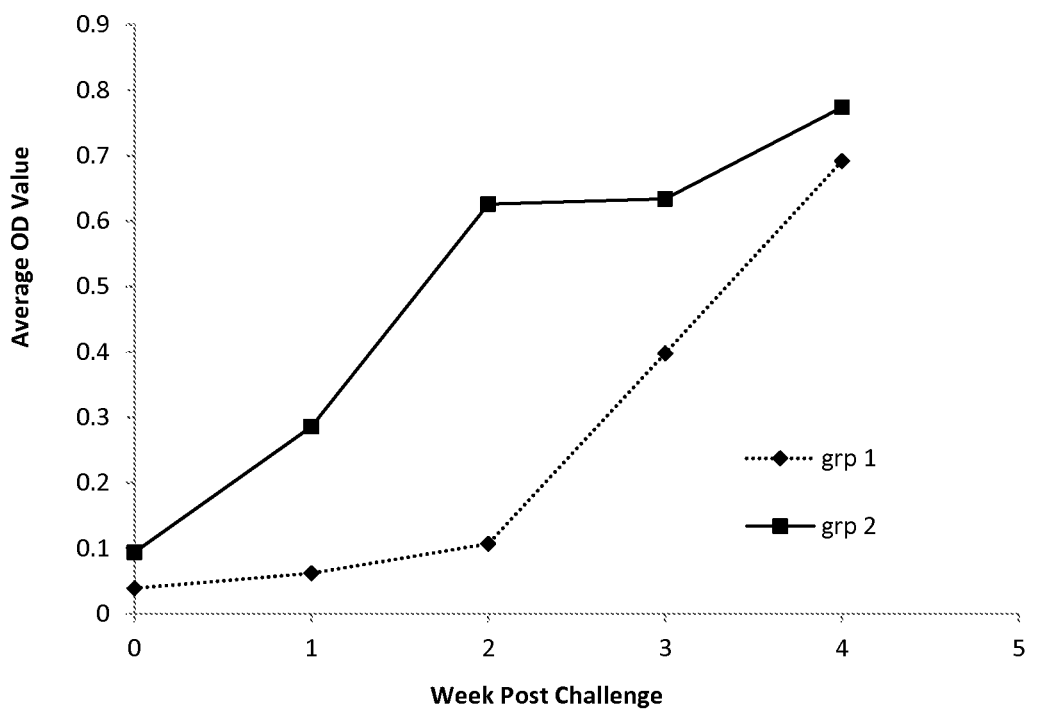
FIG. 1 is a graph showing the average ELISA OD values of Group 1 (placebo) and Group 2 (vaccinates) for PCV2 specific antibody post challenge with PCV2.

Vaccine systems for combined protection against PCV2 and *M. hyopneumoniae* have been developed. However, these vaccines generally require a complex vaccination process that includes multiple steps and/or doses which require additional labor and costs. In one commercial system, the PCV2 vaccine and *M. hyopneumoniae* vaccine are provided in separate bottles and require a mixing step before administration. After mixing, the combined vaccine preparation has limited stability and must be administered to pigs within a limited time period, generally no more than 4 hours after mixing. The mixing step introduces risk of contamination and requires additional labor compared to a ready-to-use (RTU) vaccine. Vaccines containing both PCV2 antigens and *M. hyopneumoniae* antigen premixed in a single bottle have also been developed. However, these premixed vaccines generally require a two dose vaccination regime to elicit protective immunity—a priming vaccination within the first several weeks after birth and a booster vaccination around the time of weaning—and therefore do not decrease the number of injections or simplify the vaccination process. Many of the two bottle vaccine systems also require a similar two dose vaccination regime to elicit protective immunity.

A multivalent immunogenic composition comprising PCV2 ORF2 capsid antigen and *M. hyopneumoniae* antigen is disclosed. The immunogenic composition can suitably be formulated as a multivalent vaccine, in particular a ready-to-use (RTU) vaccine. The RTU vaccine of the disclosure is provided in a pre-mixed form in a single bottle to simplify the vaccination process and does not require additional mixing steps typical of conventional two bottle vaccine systems or a priming vaccination and follow-up booster vaccination to elicit protective immunity. A single dose of the RTU vaccine of the disclosure elicits an immune response in vaccinated pigs and is efficacious against *M. hyopneumoniae* and PCV2 infections. A single dose of the RTU vaccine disclosed herein has been found to reduce or prevent viremia caused by PCV2, reduce or prevent virus colonization of lymphoid tissues, reduce or prevent lymphoid depletion associated with PCV2, reduce or prevent clinical signs associated with PCV2 infection such as wasting, paleness of the skin, respiratory distress, diarrhea, and/or jaundice, and/or reduce or prevent lung lesions caused by *M. hyopneumoniae* infection.

I. Definitions

Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and not intended to be limiting. The term "such as" also is not intended to be limiting. For example, the term "including" shall mean "including, but not limited to."

The term "immunogenic" as used herein means capable of producing an immune response in a host animal against an antigen or antigens. This immune response forms the basis of protective immunity elicited by an immunogenic composition, such as a vaccine, against a specific infectious organism, such as PCV2 or *M. hyopneumoniae*.

The term "vaccine" as used herein refers to an immunogenic composition comprising one of more antigens which, when administered to a mammal, such as a pig, induces or stimulates or elicits cellular or humoral immune responses to the one or more antigens of the vaccine. A vaccine may contain an adjuvant to produce a more robust immune response in the host animal to the one or more antigens.

The term "adjuvant" as used herein refers to a substance used in combination with an antigen or combination of antigens to produce a more robust immune response in a mammal, such as a pig, than the antigen or combination of antigens alone.

"Stimulating an immune response", "inducing an immune response" and "eliciting an immune response" are used interchangeably unless stated otherwise and include, but are not limited to, inducing, stimulating, or eliciting a therapeutic or prophylactic effect that is mediated by the immune system of an mammal, such as a pig. More specifically, stimulating an immune response in the context of the invention refers to eliciting cellular or humoral immune responses, thereby inducing downstream effects such as production of antibodies, antibody heavy chain class switching, maturation of APCs, and stimulation of cytolytic T cells, T helper cells and both T and B memory cells to the one or more antigens of the vaccine.

"Antigen" as used herein refers to a substance that induces a specific immune response in a host animal, such as a pig. The antigen may comprise a whole microorganism or virus, a subunit of a microorganism or virus, a peptide, polypeptide, glycoprotein, carbohydrate, hapten, and combinations thereof capable of inducing an immune response upon presentation in a host animal in the presence and/or absence or an adjuvant.

The term "multivalent" as used herein refers to an immunogenic composition or vaccine comprising one or more PCV2 antigens and one or more *M. hyopneumoniae* antigens.

II. Exemplary Embodiments

Various embodiments will be described in detail with reference to the drawings and tables. Reference to various embodiments does not limit the scope of the claims attached hereto. Additionally, any examples set forth in this specification are not intended to be limiting and merely set forth some of the many possible embodiments.

A multivalent immunogenic composition comprising PCV2 ORF2 capsid antigen and *M. hyopneumoniae* antigen is disclosed. The immunogenic composition can suitably be formulated as a multivalent vaccine, in particular a ready-to-use (RTU) vaccine. A single dose of the RTU vaccine of the disclosure comprises a premixed formulation containing an immunogenic amount of PCV2 antigen, an immunogenic amount of *M. hyopneumoniae* antigen, and a two component adjuvant system.

The PCV2 antigen comprises PCV2 ORF2 capsid antigen. The antigen can be produced by way of a recombinant viral vector comprising one or more PCV2 ORF2 nucleotide coding sequences under control of a suitable promoter, wherein PCV2 ORF2 capsid protein is expressed by the recombinant viral vector. Suitable cells are infected with the recombinant viral vector, the infected cells are cultured and the recombinant ORF2 capsid antigen is expressed by the infected cells. Preferably, the cells secrete the recombinant antigen into the supernatant for ease of recovery, although the recombinant antigen can also be recovered from the cells using conventional methods.

The PCV2 ORF2 nucleotide sequence can be amplified from PCV2, preferably a virulent PCV2, using PCR. Primers for amplifying PCV2 ORF2 are disclosed in the examples below. The nucleotide sequence for PCV2 ORF2 is known and primers for amplifying the nucleotide sequence can be identified and constructed using conventional methods. The amplified PCV2 ORF2 nucleotide sequence can be transferred into a suitable shuttle vector and the portion of the shuttle vector comprising the heterologous PCV2 ORF2 nucleotide sequence can transfected into a suitable viral vector. See for example U.S. Pat. No. 8,008, 001 and U.S. Pat. No. 8,119,143.

Preferred viral vectors include baculovirus although it is understood that other viral expression systems are suitable. Baculovirus expression vectors produce high levels of viral antigen in insect cells, including but not limited to *Spodoptera* cells, *Trichoplusia* cells, and High Five cells, eliminating the need for complicated and time consuming procedures to concentrate the antigen from infected cells. Examples of suitable *Spodoptera* cells include but are not limited to Sf-9 cells and Sf-21 cells. Examples of suitable *Trichoplusia* cells include but are not limited to T.ni cells. Baculovirus expression systems are commercially available from many different companies, including the Bac-to-Bac HBM TOPO® baculovirus expression system (Invitrogen, Carlsbad, Calif.) described in the examples below. Additional examples of suitable expression systems include the BaculoDirect™ and Bac-to-Bac® baculovirus expression systems (Invitrogen, Carlsbad, Calif.) and BacPAK™ baculovirus expression systems (Clontech, Mountain View, Calif.).

In the baculovirus vector, the PCV2 ORF2 nucleotide sequence is placed under the control of a suitable promoter. For example, a PCV2 ORF2 nucleotide sequence can be placed under the control of the $P_H$ promoter or $P_{10}$ promoter. In an embodiment, a PCV2 ORF2 nucleotide sequence is inserted into an insertion site in the $P_{10}$ locus and/or in the $P_H$ locus of the baculovirus genome. In this manner, a vector comprising two copies of the PCV2 ORF2 nucleotide sequence can be constructed to enable high amounts of antigen production by the infected cells. Other suitable promoters, either heterologous or heterogeneous, known to one of skill in the art may be used. A detailed description of baculovirus expression vector systems and cell culture conditions and techniques for producing recombinant protein using such an expression system can be found, for example, in Hitchman et al., 2009, Baculovirus Expression Systems for Recombinant Protein Production in Insect Cells, *Rec. Pat. Biotechnol.*, 3:46-54 a review article describing major developments and patents relating to baculovirus expression systems since the initial use of baculovirus as an expression tool and Guide to Baculovirus Expression Vector Systems (BEVS) and Insect Cell Culture Techniques published by Invitrogen (Carlsbad, Calif.), accessible at http://tools.invitrogen.com/content/sfs/manuals/bevtest.pdf.

The PCV2 ORF2 capsid antigen can be concentrated and purified from the cell culture using conventional methods. In an embodiment, the PCV2 ORF2 capsid antigen is concentrated and purified from the cell culture by filtration and then centrifugation. In embodiments, the cell culture is centrifuged at 5,000×g for at least 20 minutes. The supernatant is retained as it contains PCV2 ORF2 capsid antigen secreted by the cells. The pellet which contains cells and cell debris is then resuspended in a buffer, such as a phosphate buffer, and subjected to one or more freeze-thaw cycles, preferably 2 to 3 freeze-thaw cycles, to release PCV2 ORF2 capsid antigen from the cells. The pellet can optionally be frozen prior to resuspending the pellet in the buffer. Preferably the cells suspended in the buffer are frozen for about 5 minutes to about 24 hours before being allowed to thaw. In an embodiment, the frozen cells are thawed at a temperature of about 37° C. The material can be centrifuged after each freeze-thaw cycle and the supernatant retained. The supernatants can then be pooled with the supernatant from the initial filtration and centrifugation to provide concentrated and purified PCV2 ORF2 capsid antigen.

In embodiments, the RTU vaccine comprises at least about 1 ELISA unit of recombinant PCV2 ORF2 capsid antigen per dose. One ELISA unit is the minimum protective dose of capsid antigen in the host animal (e.g., a pig), as further described in Example 2. To determine ELISA units, a standard curve for a reference PCV2 ORF2 capsid antigen is established by serially diluting the reference antigen and detecting the antigen with a standardized concentration of monoclonal anti-PCV2 antibody. One example of a reference antigen is PCV2-Ag-51811. Anti-PCV2 antibodies are commercially available, for example, from RTI (Brookings, S. Dak.). Once the ELISA units of the reference antigen are determined, the standard curve can be used for dose determination for all samples tested by ELISA against the reference antigen.

In embodiments, the vaccine comprises at least about 1 ELISA unit to about 5 ELISA units, about 1 ELISA unit to about 4 ELISA units, about 1 ELISA unit to about 3 ELISA units, about 1 ELISA unit to about 2 ELISA units of PCV2 ORF2 capsid antigen per dose. In another embodiment, the vaccine comprises about 1 ELISA unit PCV2 ORF2 capsid antigen per dose. A dose of the vaccine of the disclosure is generally about 0.5 ml to about 2.0 ml. In an embodiment, a dose of the vaccine is about 1.0 ml to about 2.0 ml, about 1.0 ml to about 1.75 ml, about 1.0 ml to about 1.5 ml, or about 1.0 ml to about 1.25 ml. In an embodiment, a dose of the vaccine comprises about 1.0 ml.

The *M. hyopneumoniae* antigen comprises inactivated (whole cell or disrupted) or a lysate or sonicate of an inactivated, attenuated, or virulent *M. hyopneumoniae*. In some embodiments, the lysate or sonicate comprises a whole cell lysate or sonciate, or a fraction thereof comprising cell membrane and/or a protein fraction of the lysate or sonicate. In some embodiments, the *M. hyopneumoniae* antigen comprises disrupted *M. hyopneumoniae*. In other embodiments, the *M. hyopneumoniae* antigen comprises a sonicate of *M. hyopneumoniae*. In some embodiments, the RTU vaccine comprises at least about 60 micrograms per dose. In some embodiments, the vaccine comprises about 60 micrograms to about 200 micrograms, about 60 micrograms to about 180 micrograms, about 100 micrograms to about 200 micrograms, about 100 micrograms to about 180 micrograms, about 100 micrograms to about 160 micrograms, about 100 micrograms to about 140 micrograms of *M. hyopneumoniae* antigen per dose. In an embodiment, the vaccine comprises at least 120 micrograms of *M. hyopneumoniae* antigen per dose. In yet another embodiment, the vaccine comprises about 120 micrograms of *M. hyopneumoniae* antigen per dose.

The first component of the adjuvant system comprises a saponin based adjuvant. Examples of suitable saponins include but are not limited to *Quilaja* saponins, *Ginseng* saponins, *Panax notoginseng* saponins, *Platycodon grandiflorum* saponins, *Astragalus* saponins, *Achyranthes* saponins, and *Polygala* saponins. Other saponins useful as adjuvants are known and described for example in Sun et al., 2009, *Vaccine,* 27:1787-1796 which is incorporated herein by reference. In an embodiment, the saponin comprises Quil A saponin or a derivative thereof including but not limited to QS-7, QS-17, QS-18, QS-21, or a combination thereof. Saponins can also be described on the basis of the number and position of sugar chains. The saponin used in the adjuvant system described herein can be a type 3-monodesmoside (MD); 3,28-bisdesmoside (BD); 3,6(25)-BD; 3,21-BD; 3,22-BD; 3,26-BD; or 3,6,25-tridesmoside (TD) saponin. In certain embodiments, the saponin comprises a type 3-MD saponin. In some embodiments, the vaccine comprises about 50 to about 200 micrograms saponin per dose. In an embodiment, the vaccine comprises about 75 to about 150 micrograms saponin per dose. In another embodiment, the vaccine comprises about 90 to about 110 micrograms saponin per dose. In yet another embodiment, the vaccine comprises about 100 micrograms saponin per dose.

The second component of the adjuvant system comprises an oil-in-water (O/W) emulsion adjuvant or aluminum adjuvant. Any suitable oil may be used in the O/W adjuvant, such as a mineral oil or non-mineral oil. The oil phase may contain a mixture of different oils, either mineral or non-mineral. The O/W adjuvants generally comprise from about 25% to about 60% oil phase and about 40% to about 75% water phase. Examples of suitable 0/W emulsion adjuvants include but are not limited to AS03 and AS03 (GSK), MF59 (Novartis), AF03 (Sanofi Pasteur), Montanide (Seppic), Lipovant, AddaVax (InvivoGen), Trigen (Newport Laboratories, Worthington, Minn.), Adjuvant 65. In embodiments, the vaccine comprises about 5% to about 45% v/v O/W adjuvant. In an embodiment, the vaccine comprises about 10% to about 40% v/v O/W adjuvant.

The aluminum adjuvant comprises an aluminum salt or gel comprising aluminum salt. The aluminum salt can be aluminum hydroxide, aluminum phosphate, aluminum potassium sulfate, or a mixture thereof. In embodiments, the aluminum salt comprises $Al_2(OH)_3$. Examples of aluminum adjuvants include but are not limited to aluminum hydroxide gel. In embodiments, the vaccine comprises about 5% to about 45% v/v aluminum adjuvant. In an embodiment, the vaccine comprises about 10% to about 40% v/v aluminum adjuvant.

The RTU vaccine can further include one or more suitable preservatives. Examples of suitable preservatives include but are not limited to thimerosal and antibiotics. Examples of antibiotics include but are not limited to penicillin, streptomycin, and amphotericin B. In an embodiment, the vaccine comprises from about 10 to about 200 unit of penicillin per ml. In another embodiment, the vaccine comprises from about 10 to about 200 microgram streptomycin per ml. In yet another embodiment, the vaccine comprises about 0.1 to about 1.0 microgram amphotericin B per ml. In embodiments, the vaccine comprises about 0.005% to about 0.01% by weight of a preservative. In an embodiment, the preservative comprises thimerosal.

The vaccine of the disclosure generally includes a physiologically acceptable vehicle. A "physiologically acceptable" vehicle is any vehicle that is suitable for in vivo administration (e.g., oral, transdermal, or parenteral administration) or in vitro use, i.e., cell culture. Suitable physiologically acceptable vehicles for in vivo administration include water, buffered solutions, and glucose or dextrose solutions, among others. A suitable vehicle for cell culture is commercially available cell culture media. Additional components of the vaccine may suitably include excipients such as stabilizers, preservatives, diluents, emulsifiers or lubricants, in addition to the physiologically acceptable vehicle. In particular, suitable excipients include, but are not limited to, Tween 20, NP-40, DMSO, sucrose, L-histidine, polysorbate 20, and serum.

As appreciated by skilled artisans, the vaccine disclosed herein can be suitably formulated to be compatible with the intended route of administration. Examples of suitable routes of administration include parenteral, e.g., intravenous, intradermal, intramuscular, subcutaneous, oral (e.g., inhalation), transdermal (topical), transmucosal, and rectal administration. A suitable route of administration to swine is intramuscular. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The pH of the composition can be adjusted with acids or bases, such as hydrochloric acid or sodium hydroxide. Systemic administration of the composition is also suitably accomplished by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories.

Exemplary embodiments of a RTU vaccine according to the disclosure are shown in Tables 1 and 2.

TABLE 1

| | Concentration per Dose (ml) |
|---|---|
| *M. hyopneumoniae* antigen | ≥120 µg |
| Saponin | ≥100 µg |
| PCV2 capsid protein | ≥1 ELISA unit |
| Non-ionic detergent | ≤1% |
| Oil-in-water adjuvant | ≥10% v/v |
| Preservative | 0.005-0.01% |
| diH2O | 1 mL |

TABLE 2

| | Concentration per Dose (ml) |
|---|---|
| *M. hyopneumoniae* antigen | ≥120 µg |
| Saponin | ≥100 µg |
| PCV2 capsid protein | ≥1 ELISA unit |
| Non-ionic detergent | ≤1% |
| Aluminum adjuvant | 15% v/v |
| Preservative | 0.005-0.01% |
| diH2O | 1 mL |

The vaccine of the disclosure is provided in a pre-mixed, ready-to-use form to simplify the vaccination process and does not require additional mixing steps typical of conventional two bottle vaccine systems or a priming vaccination and follow-up booster vaccination to elicit protective immunity. In embodiments, an RTU vaccine of the disclosure is formulated by solubilizing an immunogenic amount of *M. hyopneumoniae* antigen in a non-ionic detergent. In embodiments, the concentration of the non-ionic detergent is about 0.5% to about 2% v/v. In an embodiment, the concentration of the non-ionic detergent is about 1% v/v. The solubilized *M. hyopneumoniae* antigen mixed with an amount of saponin to form a partially adjuvanted mixture. In an embodiment, a 1% w/v solution of saponin is added to the solubilized antigen at a concentration of about 50 micrograms to about 150 micrograms saponin per ml. Recombinant PCV2 ORF2 capsid antigen is solubilized in a non-ionic detergent. In embodiments, the concentration of the non-ionic detergent is about 0.5% to about 2% v/v. In an embodiment, the concentration of the non-ionic detergent is about 1% v/v. An immunogenic amount of the solubilized capsid antigen is then mixed with the partially adjuvanted mixture of *M. hyopneumoniae* antigen to form a partially adjuvanted vaccine. The partially adjuvanted vaccine is then diluted with a physiologically acceptable vehicle, such as an aqueous buffer, to the final volume and then mixed with an aluminum adjuvant or O/W adjuvant to form the RTU vaccine. Preferably, the RTU vaccine comprises at least about 120 micrograms of *M. hyopneumoniae* antigen and at least about 1 ELISA unit PCV2 ORF2 capsid antigen per dose. In embodiments, the vaccine comprises about 1 ELISA to about 5 ELISA unit of capsid antigen and about 60 micrograms to about 200 micrograms of *M. hyopneumoniae* antigen per dose. In an embodiment, the vaccine comprises about 1 ELISA to about 3 ELISA unit of capsid antigen and about 60 micrograms to about 180 micrograms of *M. hyopneumoniae* antigen per dose. In embodiments, the vaccine comprises about 50 micrograms to about 150 micrograms saponin per dose. In an embodiment, the vaccine comprises about 90 micrograms to about 120 micrograms saponin per dose.

A single dose of the RTU vaccine of the disclosure elicits an immune response in the vaccinated pig. A dose of the vaccine is generally about 0.5 ml to about 2.0 ml. In an embodiment, a dose of the vaccine is about 1.0 ml to about 2.0 ml, about 1.0 ml to about 1.75 ml, about 1.0 ml to about 1.5 ml, or about 1.0 ml to about 1.25 ml. In an embodiment, a dose of the vaccine comprises about 1.0 ml. In embodiments, the immune response elicited by a single dose of the vaccine administered to a pig reduces or prevents viremia caused by PCV2 compared to a pig that is not vaccinated or is administered a negative control before challenge with a field strain of PCV2 and/or *M. hyopneumoniae* as described in the examples below. In embodiments, the immune response elicited by a single dose of the vaccine administered to a pig reduces or prevents virus colonization of lymphoid tissues, reduces or prevents lymphoid depletion associated with PCV2 compared to a pig that is not vaccinated or is administered a negative control before challenge with a field strain of PCV2 and/or *M. hyopneumoniae* as described in the examples below. In embodiments, the immune response elicited by a single dose of the vaccine administered to a pig reduces or prevents clinical signs associated with PCV2 infection such as wasting, paleness of the skin, respiratory distress, diarrhea, and/or jaundice compared to a pig that is not vaccinated or is administered a negative control before challenge with a field strain of PCV2 as described in the examples below. In embodiments, the immune response elicited by a single dose of the vaccine administered to a pig reduces or prevents lung lesions caused by *M. hyopneumoniae* infection as compared to a pig that is not vaccinated or is administered a negative control before challenge with a field strain of *M. hyopneumoniae* as described in the examples below.

The vaccine may be administered orally, parenterally, intramuscularly, intranasally or intravenously to the pig. Oral delivery may encompass, for example, adding the compositions to the feed or drink of the pigs. In an embodiment, the vaccine is administered to the pig intramuscularly. The vaccine is generally administered to the pig within 1 to 2 weeks of birth. When the vaccine of the disclosure is administered within the first few weeks after birth, the pig may obtain immunoprotection against PCV2 by the weaning stage, which is when piglets become most susceptible to PCV2 infection.

EXAMPLES

The following examples are illustrative, and other embodiments are within the scope of the present disclosure.

Example 1

Production of PCV2 Capsid Antigen

The capsid ORF2 gene of PCV2b was expressed in the Bac-to-Bac® Baculovirus Expression System (Invitrogen, Carlsbad, Calif.). Generation of recombinant baculovirus was based on a site-specific transposition of an expression cassette into a baculovirus shuttle vector (bacmid) propagated in *E. coli*. An expression construct containing two copies of the ORF2 genes was generated using the pFast-Bac-dual donor plasmid (Invitrogen). PCV2b gene expression is controlled by baculovirus-specific promoters $P_{PH}$ and $P_{P10}$. DH10Bac *E. coli* with a baculovirus shuttle vector (bacmid) and a helper plasmid provided for the generation of a recombinant bacmid following transposition of the pFast-Bac-dual expression construct. The recombinant bacmid generated rBav-PCV2 after transfection of insect cells and capsid ORF2 protein was produced in cell cultures.

DNA Extraction from PCV2b and PCR A

DNA was extracted from a PCV2b isolate with a DNA extraction kit (Qiagen). Following the extraction of the viral DNA, PCR amplification was performed to isolate the full-length ORF2 gene of PCV2b. Four different PCR primers were designed to prepare two different inserts for $P_{PH}$ and $P_{P10}$ promoters. The ORF2 gene is 702 bp and can be detected by gel electrophoresis. The nucleotide sequence of the amplified ORF2 gene (SEQ ID NO:1) is shown below:

```
  1 ATGACGTATC CAAGGAGGCG TTACCGGAGA AGAAGACACC GCCCCCGCAG CCATCTTGGC

61 CAGATCCTCC GCCGCCGCCC CTGGCTCGTC CACCCCCGCC ACCGTTACCG CTGGAGAAGG

121 AAAAATGGCA TCTTCAACAC CCGCCTATCC CGCACCTTCG GATATACTAT CAAGCGAACC
```

```
-continued
181 ACAGTCAGAA CGCCCTCCTG GGCGGTGGAC ATGATGAGAT TCAATATTAA TGACTTTCTT

241 CCCCCAGGAG GGGGCTCAAA CCCCCGCTCT GTGCCCTTTG AATACTACAG AATAAGAAAG

301 GTTAAGGTTG AATTCTGGCC CTGCTCCCCG ATCACCCAGG GTGACAGGGG AGTGGGCTCC

361 AGTGCTGTTA TTCTAGATGA TAACTTTGTA ACAAAGGCCA CAGCCCTCAC CTATGACCCC

421 TATGTAAACT ACTCCTCCCG CCATACCATA ACCCAGCCCT TCTCCTACCA CTCCCGCTAC

481 TTTACCCCCA AACCTGTCCT AGATTCCACT ATTGATTACT TCCAACCAAA CAACAAAAGA

541 AACCAGCTGT GGCTGAGACT ACAAACTGCT GGAAATGTAG ACCACGTAGG CCTCGGCATT

601 GCGTTCGAAA ACAGTATAAA CGACCAGGAA TACAATATCC GTGTAACCAT GTATGTACAA

661 TTCAGAGAAT TTAATCTTAA AGACCCCCCA CTTAACCCTT AA
```

The PCR product of the ORF2 gene was purified by gel electrophoresis for PCR subcloning. The sequence of the primers is shown in Table 3.

TABLE 3

| Primer | Sequence | SEQ ID NO: |
|---|---|---|
| BHPCV2bF | ATATATGGATCCATGACGTATCCAAGGAGGCGTTACCG | 2 |
| HDPCV2bR | GATCGCAAGCTTTTAAGGGTTAAGTGGGGGGTCTTTAAGA | 3 |
| XHPCV2bF | ATTATACTCGAGATGACGTATCCAAGGAGGCGTTACCG | 4 |
| KPPCV2bR | GCTCACGGTACCTTAAGGGTTAAGTGGGGGGTCTTTAAGA | 5 |

Subcloning of the ORF2 Gene into Shuttle Vector pCR2.1 TOPO

The PCR product of the ORF2 gene of PCV2b was cloned into pCR2.1 TOPO vector directly (Invitrogen, Carlsbad, Calif.). E. coli TOP 10 cells were transformed with the vector. Plasmid DNAs of recombinant pCR2.1 TOPO was extracted and purified for DNA sequencing to confirm that the ORF2 gene was in frame.

Cloning of ORF2 into Expression Vector pFastBac-Dual

Modified ORF2 gene for insertion was prepared from shuttle vector pCR2.1 TOPO by restriction endonuclease digestion. First, pFastBac-dual and pCR2.1TOPO-ORF2(B/H) were digested with BamHI and HindIII for cloning the ORF2 into $P_{PH}$ promoter. Recombinant pFastBac-dual-ORF2(B/H) was picked up for further processing. Second, recombinant pFastBac-Dual-ORF2(B/H) and pCR2.1TOPO-ORF2(X/K) were digested with XhoI and KpnI for cloning ORF2 into $P_{P10}$ promoter. After screening and recombinant clone confirmation, the two copies of the ORF2 genes were inserted into pFastBac-Dual for production of recombinant baculovirus.

*E. coli* Mech T1 chemical competent cells (Invitrogen) were transformed with the plasmid DNAs of recombinant pFastBac-dual. Recombinant pFastBac-dual with ORF2 gene was selected on LB agar plate with ampicillin (100 μg/mL). Insertion of the ORF2 gene was confirmed with either restriction endonuclease digestion or PCR amplification. The digestion of BamHi/HindIII or XhoI/KpnI released the ORF2 gene from the pFastBac-dual vector.

Generating Recombinant Bacmid

After the recombinant pFastBac-Dual construct with ORF2 gene was generated, the purified plasmid DNA was transformed into DH10Bac *E. coli* cells to produce a recombinant bacmid by transposition. MAX Efficiency DH10Bac chemically competent cells (Invitrogen, Carlsbad, Calif.) were used for transformation of recombinant pFastBac-dual and the blue/white colony selection was used to identify colonies containing the recombinant bacmid. Recombinant bacmid was also selected on an LB agar plate containing 50 μg/mL kanamycin, and 7 μg/mL gentamicin. After incubating the plate for 48 hrs at 37° C., the largest, most isolated white colonies were picked up for further screening.

White colonies (10) were picked and restreaked onto fresh LB plates containing 50 μg/mL kanamycin, 7 μg/mL gentamicin, 10 μg/mL tetracycline, 100 μg/mL Bluo-gal, and 40 μg/mL IPTG. From a single white colony, a liquid culture containing 50 μg/mL kanamycin, 7 μg/mL gentamicin, and 10 μg/mL tetracycline was grown for isolation of recombinant bacmid DNA with the S.N.A.P. MiniPrep Kit (Invitrogen, Carlsbad, Calif.). The recombinant bacmid DNA was analyzed by PCR amplification.

The bacmid contained M13 Forward (−40) and M13 Reverse priming sites flanking the mini-attTn7 site within the lacZ α-complementation region of bacmid which can be used to facilitate PCR analysis. To verify the presence of the ORF2 gene in the recombinant bacmid, either pUCM13 Forward (−20) and pUCM13 Reverse primers or a combination of the pUCM13 Forward (−20) or pUCM13 Reverse primer and a primer that hybridizes with ORF2 gene were used. Multiple PCR amplifications were performed to verify that the recombinant bacmid with two copies of ORF2 genes was inserted into the genome of baculovirus. pUCM13F/XHORF2bR PCR was performed to validate that the ORF2 gene was inserted between $P_{P10}$ and HSVtk pA. The PCR product was approximately 2.4 kb. pUCM13R/BHORF2bF PCR was performed to validate that the ORF2 gene was inserted between $P_{PH}$ and SV40 pA. The PCR product was approximately 1.2 kb.

Generating Recombinant Baculovirus by Transfection of Insect Cells

The recombinant bacmid (rBacmid) containing the ORF2 gene was used to transfect Sf9 (*Spodoptera frugiperda*) insect cells to produce recombinant baculovirus with the ORF2 gene. Transfection was performed in a 6-well plate with 1×10⁶ cells/well. For each transfection sample, bacmid DNA and Cellfectin Reagent complexes were prepared in 12×75 mm sterile tubes as follows:

Solution A: 100 μl culture medium (SF-900 II SFM medium; Invitrogen, Grand Island, N.Y.)+9.0 μl (cellfectin reagent)

Solution B: 100 μl culture medium+rBacmid DNA (1.5-12 μg)

Solution A and Solution B were combined and incubated for 30 minutes at 20° C.+/−5° C. 0.8 mL of SF-900 medium was added to each tube before adding the complexes into Sf9 cells. The DNA:cellfectin complexes were transferred into Sf9 cells and incubated for 5 hrs in 27° C.+/−1° C. The transfection complexes were removed from cell culture and fresh cell culture added. The transfected cells were incubated at 27° C. for generation of recombinant baculovirus.

Recombinant baculoviruses (rBav) produced from transfection of Sf9 cells were released into the medium at 4 to 5 days post-transfection. Once the Sf9 cells appeared infected, the viruses were harvested from the cell culture medium by centrifugation at 500×g for 10 minutes to remove cells and large debris. The rBav was then amplified by 4 passages in Sf9 cells.

T.ni (*Trichoplusia ni*) cells (Allele Biotechnology, San Diego, Calif.) were infected with rBAV PCV2 at a MOI of about 0.05 to about 0.2 and cultured in Express Five SFM medium (Invitrogen, Carlsbad, Calif.). The cell culture was incubated at 27° C.+/−1° C. with aeration and agitation. When the cell density reached between 1-6×10⁶, fresh cell culture media was added to adjust the cell density to 1-5×10⁵. Media was added approximately every 2-6 days. The time from inoculation to harvest of the cells ranged from 6 to 12 days.

The harvested culture was concentrated and purified by filtration and then centrifugation. The harvest was filtered through a 10 kd filter. When concentrated to approximately ⅙ of the original volume, the concentrated harvested material was transferred to centrifugation tubes, centrifuged at 5,000×g for 45 minutes, and the supernatants retained. PB buffer (0.1 M phosphate buffer, pH 6.9) was added to the centrifuge tubes containing the pellets ¹/₅₀ of the original volume and the tubes were subjected to three freeze and thaw cycles to release the PCV2 capsid antigen from the T.ni cells. Freezing was accomplished in either a ≤−75° C. freezer or in an ethanol/dry-ice bath. The contents in the tube were frozen for 5 minutes to 24 hours. Thawing was done in a 37° C.±1° C. water bath.

The supernatants containing the PCV2 capsid antigen from the concentration by centrifugation and freeze-thaw procedure were inactivated with binary ethyleneimine (BEI) at 20° C.±3° C. with constant mixing for 48-72 hours. The BEI was then inactivated with 2M sodium thiosulfate at 20° C.±3° C. with constant mixing for 2-18 hours.

Example 2

Production of a First Embodiment of a Ready-To-Use Vaccine

An isolate of *Mycoplasma hyopneumoniae* was cultured and harvested when the culture reached a bacterium concentration of about 1×10⁷ CCU/ml culture medium. The harvested cells were washed three times in Tris-sodium chloride (TN) buffer [10 mM Tris-(hydroxymethyl)-aminomethane; 140 mM NaCl], pH 7.2 and 7.4 and then concentrated by centrifugation. The harvested cells were inactivated by sonic disruption with a sonicator. The antigen concentration was adjusted to 2 to 3 mg per ml with TN buffer, solubilized with a non-ionic detergent, and then a proportional amount of Quil-A saponin was added to the solubilized antigen. Merthiolate was then added to the mixture from about 1:10,000 to about 1:20,000 of the final vaccine volume to form a partially adjuvanted mixture. The partially adjuvanted mixture contained at least 120 μg of the processed and concentrated *M. hyopneumoniae* and about 100 micrograms of saponin per ml.

Inactivated PCV2 capsid antigen was produced as described in Example 1. 1% v/v NP-40 was added to the antigen and the mixture was stirred for 2 hours at room temperature to solubilize the antigen. A sample was removed for dose determination by ELISA. The reference antigen for the ELISA was PCV2-Ag-05181. A standard curve was established for the reference antigen by serially diluting the reference antigen and detecting the antigen with monoclonal anti-PCV2 antibody (RTI, Brookings, S.D.) at a concentration of 0.4 μg/ml. One ELISA unit was defined as the minimum protective dose of PCV2 capsid antigen, as determined by PCV2 vaccination and challenge, as described for example in Examples 4 and 6. The reference antigen contained 4 ELISA units/ml. Once the ELISA units of the reference antigen were determined, the number was used for dose determination for all samples tested by ELISA against the reference antigen. The partially adjuvanted *M. hyopneumoniae* mixture was then mixed with the PCV2 capsid antigen in a proportion of 120 μg of the processed and concentrated *M. hyopneumoniae* to 1 ELISA unit of PCV2 capsid antigen. The solution was mixed for at least one hour and then TN buffer was added to dilute the solution to the final volume and Trigen adjuvant was added to 15% v/v of the final volume to provide a vaccine having 15% v/v Trigen and 100 μg saponin per ml. The vaccine was mixed for at least 2 hours and then stored at 2-7° C. Table 4 shows an exemplary formulation of the ready-to-use vaccine.

TABLE 4

|  | Minimum Final Concentration per Dose (ml) |
| --- | --- |
| *M. hyopneumoniae* antigen/ Quil-A complex | 120 μg *M. hyopneumoniae* + 100 μg quil-A |
| PCV2 capsid protein | 1 ELISA unit |
| Nonidet P-40 | ≤1% |
| Trigen | 15% v/v |
| Tris (in TN buffer) | 1.08 mg |
| Sodium chloride (in TN buffer) | 7.36 mg |
| Thimerosal | 0.005-0.01% |
| diH2O | 1 mL |

Example 3

Production of a Second Embodiment of a Ready-To-Use Vaccine

A partially adjuvanted mixture containing at least 120 μg of the processed *M. hyopneumoniae* was prepared as described in Example 2. The partially adjuvanted *M. hyopneumoniae* mixture was then mixed with the PCV2 capsid antigen in a proportion of 120 μg of the processed and concentrated *M. hyopneumoniae* to 1 ELISA unit of PCV2 capsid antigen. The solution was mixed for at least one hour and then TN buffer was added to dilute the solution to the final volume and Montadine Gel 01 (SEPPIC) was added to 15% v/v of the final volume to provide a vaccine having 15% v/v gel and 100 saponin per ml. The vaccine was mixed for at least 2 hours and then stored at 2-7° C. Table 5 shows an exemplary formulation of the ready-to-use vaccine.

TABLE 5

|  | Minimum Final Concentration per Dose (ml) |
| --- | --- |
| M. hyopneumoniae antigen/ Quil-A complex | 120 µg M. hyopneumoniae + 100 µg quil-A |
| PCV2 capsid protein | 1 ELISA unit |
| Nonidet P-40 | ≤1% |
| Montadine Gel 01 | 15% v/v |
| Tris (in TN buffer) | 1.03 mg |
| Sodium chloride (in TN buffer) | 6.95 mg |
| Thimerosal | 0.005-0.01% |
| diH2O | 1 mL |

Example 4

Efficacy of a Single Dose of Ready-To-Use Vaccine in Piglets Against PCV2 Challenge A determination of the efficiency of the ready-to-use vaccine of Example 2 in piglets was conducted in two studies. The first study demonstrated the efficacy of a single 1 ml dose of the vaccine of Example 2 against field-isolated virulent PCV2 challenge. The second study (Example 5) demonstrated the efficacy of a single 1 ml dose of the vaccine of Example 2 against M. hyopneumoniae challenge. These studies show that a single 1 ml dose of the vaccine of Example 2 is efficacious against M. hyopneumoniae and PCV2 infections in piglets.

Forty-six Caesarian Derived, Colostrum Deprived (CDCD) piglets (mixed sex, age 12 days +/−1 day) were randomly divided into the following three treatment groups as shown in Table 6.

TABLE 6

| Group | Description | No. of Piglets | Treatment | ID Numbers |
| --- | --- | --- | --- | --- |
| 1 | Placebo control | 21 | Intramuscular (IM) injection of one 1 mL dose of PMT placebo | 2, 4, 6, 7, 10, 11, 14, 17, 18, 33, 34, 37, 41, 42, 43, 45, 47, 48, 76, 98 and 102 |
| 2 | Vaccinates | 21 | Intramuscular (IM) injection of one 1 mL dose of PCV2- Mycoplasma Hyopneumoniae vaccine | 1, 3, 5, 8, 9, 12, 13, 15, 16, 35, 36, 38, 39, 40, 44, 46, 82, 101, 103, 104 and 105 |
| 3 | Non-vaccinated, non-challenged environmental controls | 4 | No injection | 22, 30, 49 and 93 |

The piglets in Group 1 and Group 2 were vaccinated with a 1 ml dose of placebo control or the ready-to-use PCV2-M. hyopneumoniae vaccine according to Example 2, respectively. All the piglets were observed daily during the study period and blood samples were collected from the piglets in Groups 1, 2, and 3 on day 0 and weekly throughout the study period. The piglets were observed daily for any abnormalities in respiratory (0=normal; 1=panting/rapid; 2=dyspnea), behavior (0=normal; 1=mild to moderately lethargic; 2=severely lethargic or recumbent), body condition (0=normal; 1=mild loss of body condition; 2=moderate/severe loss of body condition) and injection site from day 0 to day 27 (data not shown). No injection site reactions were observed from any piglets. Two of the piglets from the placebo group and two piglets from the vaccine group had clinical abnormalities during the observation period but necropsy of these animals provided no evidence that the vaccine and/or vaccination caused any adverse reactions in the host animal.

Prechallenge serum samples were collected from piglets in the placebo group (Group 1) and the vaccine group (Group 2) and testing for PCV2 specific antibodies in an ELISA assay. The results of this assay (data not shown) indicated that only three piglets in the vaccinated group tested positive for PCV2 specific antibody during the pre-challenge period. All others, along with the samples from the placebo group were negative for PCV2 specific antibody.

On day 31, the piglets in Groups 1, 2, and 3 were challenged by intranasal inoculation of 1 ml per nare of a PCV2 field isolate provided by Newport Laboratories (Worthington, Minn.) and 1 ml intramuscularly of a 50/50 dose of the Newport strain and PCV2 isolate P12 Jul. 7, 2006 (University of Minnesota Veterinary School, St. Paul, Minn.). The rectal temperatures of the piglets were measured and recorded on day −2, −1, 0 and daily until day 12 post challenge. Piglets in group 3 were terminated on day 28 post vaccination. All of the piglets in Groups 1 and 2 were terminated on day 59 post vaccination (4 weeks post challenge). Gross lung lesions, hypertrophy in tracheobronchial, mesenteric and sub-iliac lymph nodes and the tonsil were evaluated. The tonsil, mesenteric lymph node, and sub-iliac lymph node were examined and scored according to established procedures at the Iowa State University Veterinary Diagnostic Laboratory (ISU VDL). Each of the lymph node samples were valued and scored as the following:

Lymph Node Deletion Score:
  0=Negative
  1=Positive-mild
  2=Positive-moderate
  3=Positive-severe Lymph Node Immunohistochemistry (IHC) Score:
  0=Negative
  1=Positive, <10% of cells with PCV2 staining
  2=Positive, 10-50% cells with PCV2 staining
  3=positive, >50% of cells with PCV2 staining.

Serum samples collected on days 0, 7, 14 and 21 post vaccination were analyzed by ELISA for PCV2 specific antibodies, expressed as S/P ratio (S/P ratio <0.4 considered negative). Serum samples collected on days 31 (day of challenge), 38, 45, 52 and 59 were also analyzed by ELISA for PCV2 specific antibodies (S/P ratio of <0.3 considered negative). All samples collected on day 0 post challenge were negative for PCV2 specific antibodies. Nine samples in Group 2 became positive on day 7 post challenge. All samples from day 14, 21 and 28 in Group 2 were positive for PCV2 antibody. All day 7 and 14 post challenge samples from Group 1 were negative. The average ELISA OD values of Group 1 (placebo) and Group 2 (vaccine) shown in FIG.

1. Statistical analysis revealed that titers in the vaccinated group increased significantly over time, and the rate at which the titers increased in the vaccinated group was significantly greater than in the placebo group (data not shown).

Figure 2:
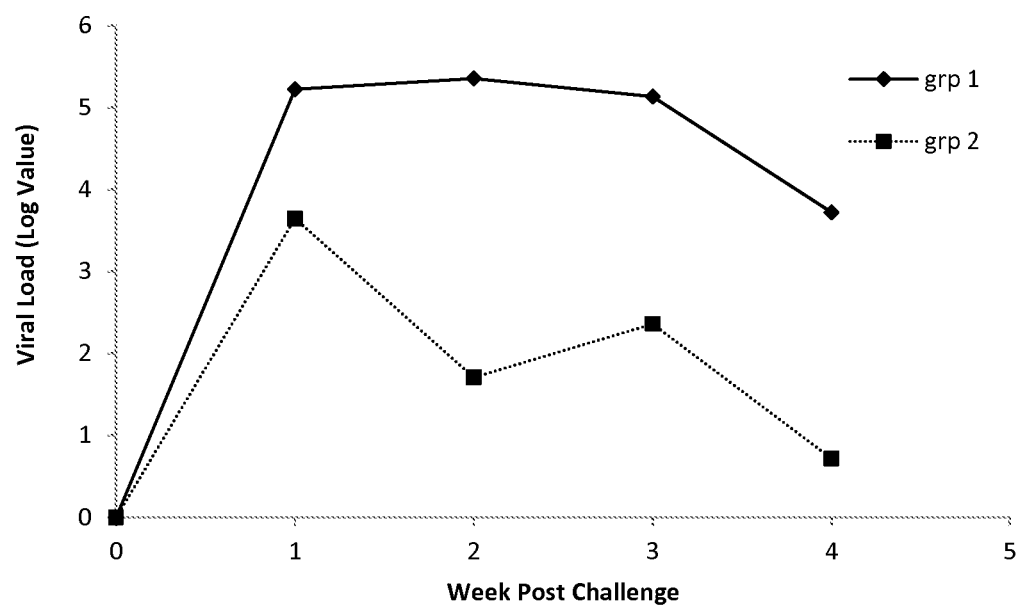
FIG. 2 is a graph showing geometric mean viral loads (Log) of Group 1 (placebo) and Group 2 (vaccinates) piglets post challenge with PCV2.

Serum samples collected on day 0, 7, 14, 21 and 28 post challenge were tested by qPCR at ISU VDL to determine the virus load. The results were expressed as the number of copies per mL in the tested samples. The geometric mean viral loads (Log) of Group 1(placebo control) and Group 2 (vaccine) are shown in FIG. 2. All samples collected on day 0 were negative. All samples in Group 1 became positive at day 7 post challenge, while all but two samples from Group 2 were positive (data not shown). In addition, 11 animals from Group 2 produced negative qPCR results on day 28 post challenge while only 1 Group 1 animal was negative on Day 28 (data not shown). The mean virus load reduction in the vaccinated group as compared to that in the placebo group was over 97% on day 7 and over 99% on days 14, 21 and 28 of post challenge. Statistical analysis revealed that viral loads in the vaccinated group (Group 2) were significantly lower than the placebo group (Group 1) on all sample dates after challenge. In addition, the rate of decrease in viral load was significantly greater in the vaccinated group than that in the placebo group (data not shown). The qPCR and ELISA results show that a single 1 ml dose of the vaccine of Example 2 reduced viremia in the piglets caused by PCV2 infection.

Figure 3:
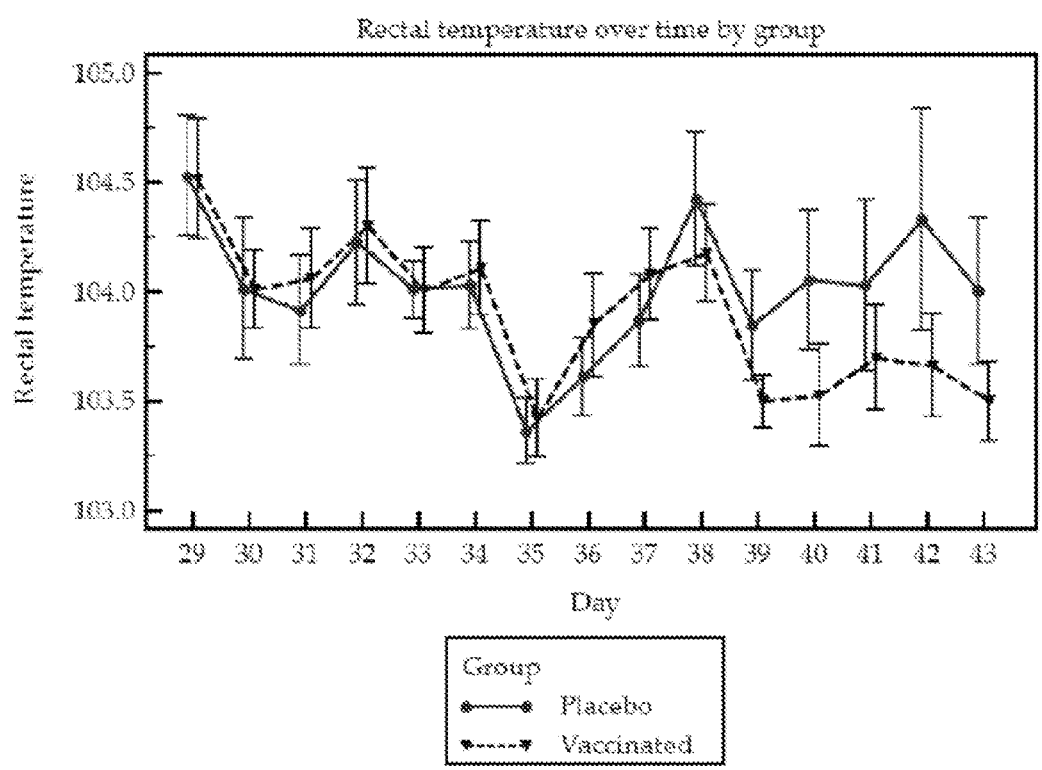
FIG. 3 is a graph showing the average rectal temperatures of Group 1 (placebo) and Group 2 (vaccinates) piglets post challenge with PCV2.

The piglets in Groups 1 and 2 were tested for temperature from day −2 to day 12 post challenge (day 29 to day 43 post vaccination). The average temperature in both Group 1 (placebo) and Group 2 (vaccine) was high on the first day of temperature taking. There were no significant differences in temperature between Groups 1 and 2 from day −2 to day 7 post challenge. The temperatures were, however, significantly higher in the placebo group (Group 1), when compared to vaccinates (Group 2), on day 8 ($p=0.015$), day 9 ($p=0.009$), day 11 ($p=0.020$) and day 12 ($p=0.009$) post challenge (data not shown). The average temperatures of Group 1 (placebo) and Group 2 (vaccine) are depicted in FIG. 3.

Gross pathology and diagnosis were performed on day 28 post challenge by Veterinary Resource, Inc. The summary of histopathology and gross pathological diagnosis are shown in Table 7 (placebo) and Table 8 (vaccinates). Thirteen out of 20 (65%) piglets in Group 1 exhibited gross pathological signs consistent with the clinical signs of PCV2 infection. Only 2 piglets in Group 2 had mild lymph node hypertrophy. This data, along with the significant temperature difference between the piglets in Group 1 (placebo) and Group 2 (vaccinates), shows that administration of a single 1 ml dose of the vaccine of Example 2 prevented virus colonization of lymphoid tissues, lymphoid depletion, and clinical signs caused by PCV2 infection in the piglets.

TABLE 7

| | Tonsil | | MLN | | ILN | | TBLN | | TOTALS IHC- | LD- | Gross Pathology and | |
|---|---|---|---|---|---|---|---|---|---|---|---|---|
| | IHC | LD | IHC | LD | IHC | LD | IHC | LD | total | total | Remarks | Diagnosis |
| 2 | 1 | 1 | 1 | 1 | 0 | 0 | 0 | 1 | 2 | 3 | No gross lesions | Normal |
| 4 | 0 | 0 | 1 | 0 | 1 | 0 | 1 | 0 | 3 | 0 | No gross lesions | Normal |
| 6 | 0 | 0 | 0 | 0 | 1 | 1 | 0 | 0 | 1 | 1 | Consolidation | Minor pneumoniae |
| 7 | 0 | 0 | 0 | 0 | 0 | 0 | 0 | 0 | 0 | 0 | No gross lesions | Normal |
| 10 | 0 | 1 | 2 | 1 | 1 | 1 | 1 | 0 | 4 | 3 | Enteritis, rounded margins on liver see lymph node scores | Enteritis, lymph node hypertrophy |
| 14 | 3 | 3 | 3 | 3 | 3 | 3 | 3 | 3 | 12 | 12 | Poor body condition, found dead | Presumptive PCV associated mortality |
| 17 | 0 | 0 | 0 | 0 | 0 | 0 | 0 | 0 | 0 | 0 | No gross lesions | Normal |
| 18 | 2 | 1 | 0 | 0 | 1 | 1 | 0 | 1 | 3 | 3 | No gross lesions | Normal |
| 33 | 1 | 0 | 0 | 1 | 1 | 2 | 1 | 2 | 3 | 5 | Umbilical hernia, consolidation, enterities, MLN congested, poor condition | Minor pneumoniae, enteritis present, poor condition suggestive of PCV infection |
| 34 | 1 | 2 | 2 | 1 | 0 | 2 | 2 | 2 | 5 | 7 | Poor body condition | loss of body condition suggestive of PCV infection |

TABLE 7-continued

| | Tonsil | | MLN | | ILN | | TBLN | | TOTALS IHC-total | LD-total | Gross Pathology and Remarks | Diagnosis |
|---|---|---|---|---|---|---|---|---|---|---|---|---|
| | IHC | LD | IHC | LD | IHC | LD | IHC | LD | | | | |
| 37 | 1 | 1 | 1 | 2 | 1 | 2 | 1 | 1 | 4 | 6 | mottled discoloration | very minor pneumoniae |
| 41 | 0 | 0 | 0 | 0 | 0 | 0 | 1 | 1 | 1 | 1 | See lymph node scores | mild lymph node hypertrophy |
| 42 | 3 | 3 | 3 | 3 | 1 | 3 | 3 | 3 | 10 | 12 | Poor body condition, icteric diffuse | generalized icterus typical of PCV infection |
| 43 | 3 | 3 | 3 | 3 | 3 | 3 | 3 | 3 | 12 | 12 | Found dead 11 May 12, small areas of mottled discoloration in lungs, MLN nodes appear enlarged and congested, mild loss of body condition | Enteritis and mild pneumoniae present, bross lesion suggest enteritis and mild pneumonia. |
| 45 | 0 | 0 | 1 | 1 | 0 | 1 | 0 | 0 | 1 | 2 | No gross lesions | Normal |
| 47 | 2 | 2 | 1 | 1 | 0 | 2 | 1 | 2 | 4 | 7 | Poor body condition, see lymph node scores | Lymph node hypertrophy, poor condition suggestive of PCV infection |
| 48 | 2 | 2 | 3 | 3 | 2 | 3 | 2 | 3 | 9 | 11 | Poor body condition, enteritis | Enteritis present |
| 76 | 1 | 0 | 1 | 2 | 1 | 1 | 1 | 1 | 4 | 4 | Mottled discoloration, poor condition | minor penumoniae and poor condition suggestive of PCV infection |
| 98 | 0 | 0 | 0 | 0 | 0 | 0 | 0 | 0 | 0 | 0 | No gross lesions | Normal |
| 102 | 0 | 0 | 0 | 0 | 1 | 1 | 0 | 0 | 1 | 1 | See lymph node scores | Lymph node hypertrophy |

MLN: mesenteric lymph node
ILN: iliac lymph node
TBLN: tracheobronical lymph node
LD: lymphoid depletion

TABLE 8

| | Tonsil | | MLN | | ILN | | TBLN | | TOTALS IHC-total | LD-total | Gross Pathology and Remarks | Diagnosis |
|---|---|---|---|---|---|---|---|---|---|---|---|---|
| ID | IHC | LD | IHC | LD | IHC | LD | IHC | LD | | | | |
| 1 | 0 | 0 | 0 | 0 | 0 | 0 | 0 | 0 | 0 | 0 | No gross lesions | Normal |
| 3 | 0 | 0 | 0 | 0 | 0 | 0 | 0 | 0 | 0 | 0 | No gross lesions | Normal |
| 5 | 0 | 0 | 0 | 0 | 0 | 0 | 0 | 0 | 0 | 0 | No gross lesions | Normal |

TABLE 8-continued

| ID | Tonsil IHC | Tonsil LD | MLN IHC | MLN LD | ILN IHC | ILN LD | TBLN IHC | TBLN LD | TOTALS IHC-total | TOTALS LD-total | Gross Pathology and Remarks | Diagnosis |
|---|---|---|---|---|---|---|---|---|---|---|---|---|
| 8 | 0 | 0 | 0 | 9 | 0 | 0 | 0 | 0 | 0 | 0 | No gross lesions | Normal |
| 12 | 0 | 0 | 0 | 0 | 0 | 0 | 0 | 0 | 0 | 0 | See lymph node scores | Mild lymph node hypertrophy |
| 13 | 0 | 1 | 0 | 0 | 1 | 1 | 0 | 0 | 1 | 2 | No gross lesions | Normal |
| 15 | 0 | 0 | 0 | 0 | 0 | 0 | 0 | 0 | 0 | 0 | No gross lesions | Normal |
| 16 | 0 | 0 | 0 | 0 | 0 | 0 | 0 | 0 | 0 | 0 | No gross lesions | Normal |
| 35 | 0 | 0 | 0 | 0 | 0 | 0 | 0 | 0 | 0 | 0 | No gross lesions | Normal |
| 36 | 0 | 0 | 0 | 0 | 0 | 0 | 0 | 0 | 0 | 0 | No gross lesions | Normal |
| 38 | 0 | 0 | 0 | 0 | 0 | 0 | 0 | 0 | 0 | 0 | No gross lesions | Normal |
| 39 | 0 | 0 | 0 | 0 | 1 | 1 | 1 | 1 | 2 | 2 | No gross lesions | Normal |
| 40 | 1 | 1 | 0 | 1 | 1 | 1 | 1 | 1 | 3 | 4 | No gross lesions | Normal |
| 44 | 0 | 0 | 0 | 0 | 0 | 0 | 0 | 0 | 0 | 0 | No gross lesions | Normal |
| 46 | 0 | 0 | 0 | 0 | 0 | 0 | 0 | 0 | 0 | 0 | No gross lesions | Normal |
| 82 | 0 | 0 | 0 | 0 | 0 | 0 | 0 | 0 | 0 | 0 | No gross lesions | Normal |
| 101 | 0 | 0 | 0 | 0 | 0 | 0 | 0 | 0 | 0 | 0 | No gross lesions | Normal |
| 103 | 0 | 0 | 0 | 0 | 0 | 0 | 0 | 0 | 0 | 0 | See lymph node scores | mild lymph node hypertrophy |
| 104 | 0 | 0 | 0 | 0 | 0 | 0 | 0 | 0 | 0 | 0 | No gross lesions | Normal |
| 105 | 0 | 0 | 0 | 0 | 0 | 0 | 0 | 0 | 0 | 0 | No gross lesions | Normal |

Tonsil (t), mesenteric lymph node (MLN), sub-iliac lymph node (SLN) and tracheobronchial lymph node (TBLN) were collected from all piglets on the day of termination. Immunohistochemical (IHC) analysis was conducted on the samples. The results are summarized in Table 9. When comparing the IHC score between the two groups, highly significant differences were found in all the examined tissues; the p-values of MLN, SLN, T, TBLN were 0.0001, 0.0034, 0.0008 and 0.0010, respectively. The individual piglet and tissue scores are shown in Tables 7 and 8.

TABLE 9

| Group | Score 0 | Score 1 | Score 2 | Score 3 | Median/mean score | P-value |
|---|---|---|---|---|---|---|
| MLN-IHC | | | | | | |
| 1 | 8 (40%) | 6 (30%) | 2 (10%) | 4 (20%) | 1/1.1 | |
| 2 | 20 (100%) | 0 | 0 | 0 | 0/0 | |
| | 28 | 6 | 2 | 4 | | 0.0001 |
| SLN-IHC | | | | | | |
| 1 | 8 (40%) | 9 (45%) | 1 (5%) | 2 (10%) | 1/0.85 | |
| 2 | 17 (85%) | 3 (15%) | 0 | 0 | 0/0.15 | |
| | 25 | 12 | 1 | 2 | | 0.0034 |
| T-IHC | | | | | | |
| 1 | 9 (45%) | 5 (25%) | 3 (15%) | 3 (15%) | 1/1 | |
| 2 | 19 (95%) | 1 (5%) | 0 | 0 | 0/0.05 | |
| | 28 | 6 | 3 | 3 | | 0.0008 |
| TBLN-IHC | | | | | | |
| 1 | 8 (40%) | 7 (35%) | 2 (10%) | 3 (15%) | 1/1 | |
| 2 | 18 (90%) | 2 (10%) | 0 | 0 | 0/0.1 | |
| | 26 | 9 | 2 | 3 | | 0.0010 |

Figure 4:
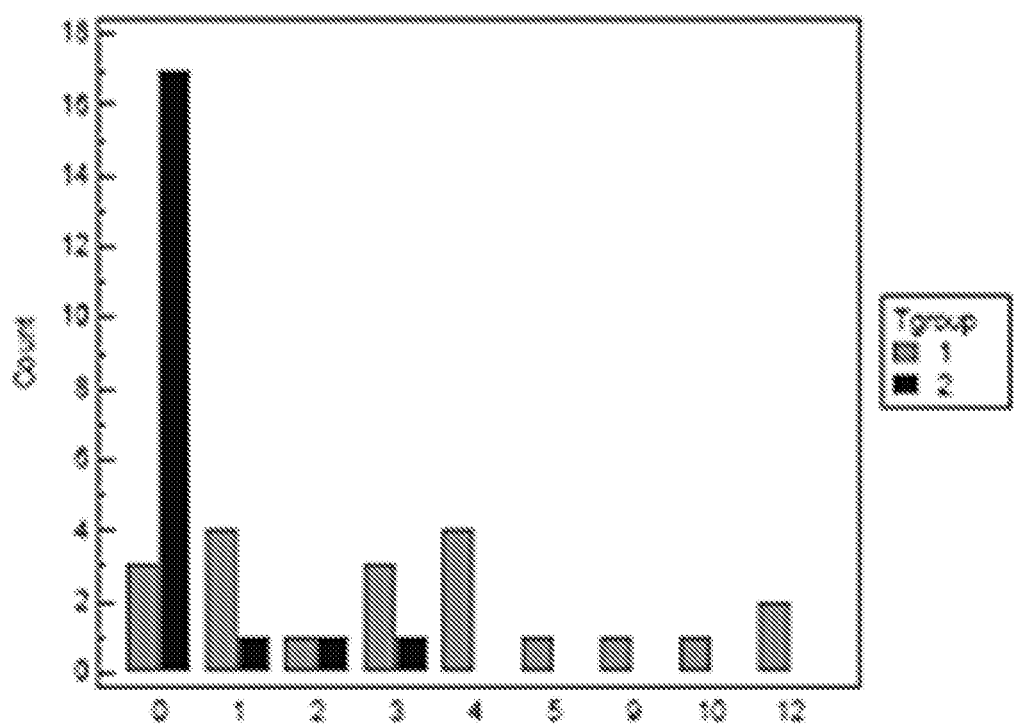
FIG. 4 is a graph showing the immunohistochemistry (IHC) score distribution upon PCV2 staining in lymph node tissue in Group 1 (placebo) and Group 2 (vaccinates) piglets post challenge with PCV2.

Seventeen out of twenty (85%) piglets in Group 2 (vaccinates) were negative in IHC tests for all examined tissues, while 17 out of 20 (85%) piglets in Group 1 (placebo) showed positive results in the IHC test. In addition, the highest total IHC score of the positive piglets in Group 2 was 3, while 12 piglets in Group 1 had a IHC score of 4 or higher (2 had max. score of 12). The IHC score distribution of Group 1 and Group 2 are shown in FIG. 4. The results in Table 9 and FIG. 4 show that a single 1 ml dose of the vaccine of Example 2 prevented virus colonization of lymphoid tissues in the piglets caused by PCV2 infection.

Figure 5:
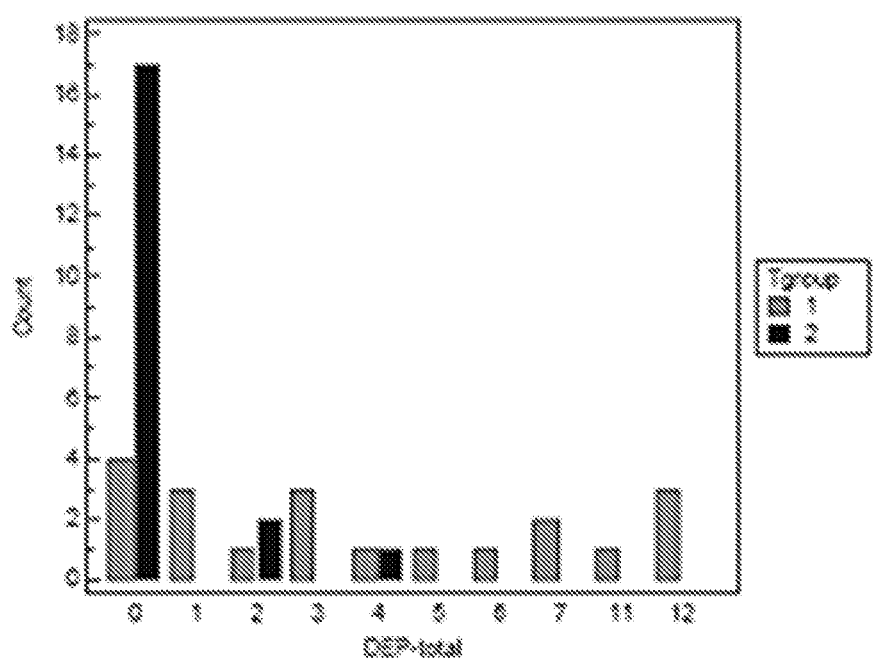
FIG. 5 is a graph showing lymphoid depletion in Group 1 (placebo) and Group 2 (vaccinates) piglets post challenge with PCV2.

When comparing the depletion scores in Groups 1 and 2, significant differences were found in all examined tissues; the p-values were 0.0003, 0.0003, 0.005 and 0.0008 for MLN, SLN, T, TBLN, respectively. Eighty percent (16 out 20) of piglets in Group 1 (placebo) had lymphoid tissue depletion scores, while 85% (17 out 20) of piglets in Group 2 (vaccinates) had no lymphoid depletion scores. Three piglets in Group 1 had the maximum score of 12. The score distribution is shown in FIG. 5. These results show that a single 1 ml dose of the vaccine of Example 2 prevented lymphoid depletion in the piglets caused by PCV2 infection.

Example 5

Efficacy of a Single Dose of Ready-To-Use Vaccine in Piglets Against *M. hyopneumoniae* Challenge A study of the efficacy of the ready-to-use vaccine of Example 2 in piglets against *M. hyopneumoniae* challenge was conducted. This study in conjunction with the PCV2 challenge study in Example 4 demonstrated that a single dose of the vaccine of Example 2 is efficacious against *M. hyopneumoniae* and PCV2 infections in piglets.

Forty-three CDCD piglets (mixed sex, age 12 days +/−1 day) were randomly divided into the following treatment groups as shown in Table 10. The piglets were *M. hyopneumoniae* antibody negative (S/P Ratio <0.4).

TABLE 10

| Group | Description | No. of Piglets | Treatment |
|---|---|---|---|
| 1 | Placebo control | 21 | Intramuscular (IM) injection of one 1 mL dose of PMT placebo |
| 2 | Vaccinates | 22 | Intramuscular (IM) injection of one 1 mL dose of PCV2-Mycoplasma *Hyopneumoniae* vaccine |

The piglets were vaccinated as shown in Table 10 and observed daily during the study for normal health. On day 33 post-vaccination, the piglets where challenged with *M. hyopneumoniae* lung inoculum (LI37), obtained from the Department of Veterinary Microbiology and Preventive Medicine, College of Veterinary Medicine, Iowa State University. All piglets were challenged intratracheally with an 18 mL inoculum. Daily observation of the piglets showed all to have normal health throughout the duration of the study, except for one piglet in the placebo group which was determined to have died of a strangulated gut.

The piglets were terminated on day 37 post challenge and necropsied to score lung lesions. The lesion scores were expressed as the percentage of the lung surface area showing gross lesions typical of enzootic pneumonia. The method for evaluating lung lesions was adapted from Pointon et al., 1999, Disease surveillance at slaughter, In: Straw, B. E., D'Allaire, S., Mengeling, W. L., Taylor, D. J. (Eds.), Diseases of Swine, 8$^{th}$ Ed., Iowa State University Press, Ames, Iowa, USA, pp. 1111-1132. The lung was divided into seven sections: left apical (0.1), right apical (0.1), left cardiac (0.1), right cardiac (0.1), left diaphragmatic (0.25), right diaphragmatic (0.25) and intermediate (0.1). The lung lesions were scored individually for each section and expressed as a percentage of the diseased lung versus the whole section. When calculating the total lung lesion score, each section was given a coefficient to represent the percentage of each section to the whole lung. The coefficients of each section are shown as the number in parenthesis above. The average lung lesion score in the vaccinated group (Group 2) was 1.727%. The average lung lesion score in the placebo group (Group 1) was 6.713%. There were 11 piglets in Group 2 that had no lung lesion, whereas, 18 out of 20 (90%) of piglets in Group 1 had lung lesions, with lesion scores ranging from 1.0% to 16.5%.

Mitigated fraction analysis revealed the lung lesions scores of the piglets in Group 1 were significantly higher than that of the piglets in Group 2. A Mitigated Fraction of 0.6409 (95% CI: 0.3523, 0.8818) was estimated when the litter effect was not considered, while a Mitigated Fraction of 0.5955 (95% CI: 0.4355, 0.7553) was estimated when the litter effect was considered. Both demonstrated that the vaccine significantly reduced the lung lesion scores in the vaccinated piglets as compared with the piglets in the placebo group.

Lung tissue samples that contained the lesions, as well as a portion of the apparently normal lung tissue adjacent to the lesions, were collected aseptically. A sample from the apical lobe was collected if there was no lesion in the lung. Each of the samples was kept in a sterile tube with 5 ml of culture media. The samples were analyzed by PCR for presence of *M. hyopneumoniae* in the sample. Five piglets in the vaccinated group (Group 2) were negative in PCR test and two of them were suspect. The rest of piglets in Group 2 were positive. In Group 1, 19 out 20 (95%) piglets were PCR positive for *M. hyopneumoniae*. The lung lesion and PCR results show that a single 1 ml dose of the vaccine of Example 2 reduces lung lesions caused by *M. hyopneumoniae* infection.

Example 6

Efficacy of a Single Dose of Ready-To-Use Vaccine in Piglets Challenged with PCV2

A study of the efficacy of the ready-to-use vaccine of Example 3 in piglets was conducted in two studies. The first study demonstrated the efficacy of a single 1 ml dose of the vaccine of Example 3 against field isolated virulent PCV2 challenge. The second study demonstrated the efficacy of a single 1 ml dose of the vaccine of Example 3 against *M. hyopneumoniae* challenge. These studies show that a single 1 ml dose of the vaccine of Example 3 is efficacious against *M. hyopneumoniae* and PCV2 infections in piglets.

Forty-six CDCD piglets (mixed sex, age 12 days +/−1 day) were randomly divided into the following three treatment groups as shown in Table 11.

TABLE 11

| Group | Description | No. of Piglets | Treatment | ID Numbers |
|---|---|---|---|---|
| 5 | Placebo control | 21 | Intramuscular (IM) injection of one 1 mL dose of PMT placebo | |
| 4 | Vaccinates | 21 | Intramuscular (IM) injection of one 1 mL dose of PCV2-Mycoplasma *Hyopneumoniae* vaccine | |
| 3 | Non-vaccinated, non-challenged environmental controls | 4 | No injection | 22, 30, 49 and 93 |

The piglets in Group 5 and Group 4 were vaccinated with a 1 ml dose of placebo control or the ready-to-use PCV2-*M. hyopneumoniae* vaccine according to Example 3, respectively. All the piglets were observed daily during the study period and blood samples were collected from the piglets in Groups 3, 4, and 5 on day 0 and weekly throughout the study period. The piglets were observed daily for any abnormalities in respiratory, behavior, body condition and injection site from day 0 to day 27 as described in Example 4. No injection site reactions were observed from any piglets. One pig from the vaccinate group (Group 4) exhibited mild clinical signs during the observation period.

On day 31, the piglets in Groups 4 and 5 were challenged by intranasal inoculation of 1 ml per nare of a PCV2 field isolate (Newport Laboratories, Worthington, Minn.) and 1 ml intramuscularly of a 50/50 dose of the Newport strain and PCV2 isolate P12 Jul. 7, 2006 (University of Minnesota Veterinary School, St. Paul, Minn.). The rectal temperatures of the piglets were measured and recorded on day −2, −1, 0 and daily until day 12 post challenge. Piglets in group 3 were terminated on day 28 post vaccination. All of the piglets in Groups 4 and 5 were terminated on day 59 post vaccination (4 weeks post challenge). Gross lung lesions, hypertrophy in tracheobronchial, mesenteric and sub-iliac lymph nodes and the tonsil were evaluated and scored as described in Example 4.

Serum samples collected on days 0, 7, 14, and 21 post vaccination were analyzed by ELISA for PCV2 specific antibodies as described in Example 4. Serum samples collected on days 31 (day of challenge), 38, 45, 52 and 59 were analyzed by ELISA for PCV2 specific antibodies as described in Example 4. Two piglets in Group 4 (vaccinates) tested positive for PCV2 specific antibody during the pre-challenge period. All others, along with the samples collected from the placebo group (Group 5) were negative.

Figure 6:
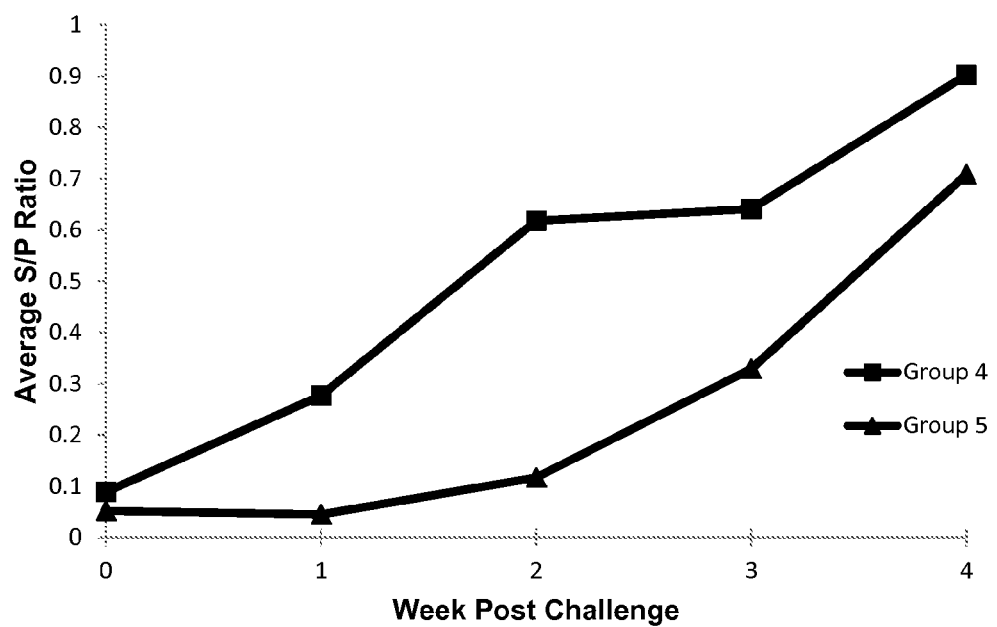
FIG. 6 is a graph showing the average S/P ratio of Group 5 (placebo) and Group 4 (vaccinates) for PCV2 specific antibody post challenge with PCV2.

All samples collected on day 0 post challenge were negative for PCV2 specific antibodies. Samples collected from the placebo group (Group 5) on day 7 and 14 post challenge were negative. Seven of the piglets in Group 4 (vaccinates) were positive on day 7 post challenge and 19 of the piglets were positive on day 14 post challenge. The average S/P ratio of Group 5 (placebo) and Group 4 (vaccinates) are shown in FIG. 6. Statistical analysis revealed that titers in the vaccinated group increased significantly over time, and the rate at which the titers increased in the vaccinated group was significantly greater than in the placebo group (data not shown).

Figure 7:
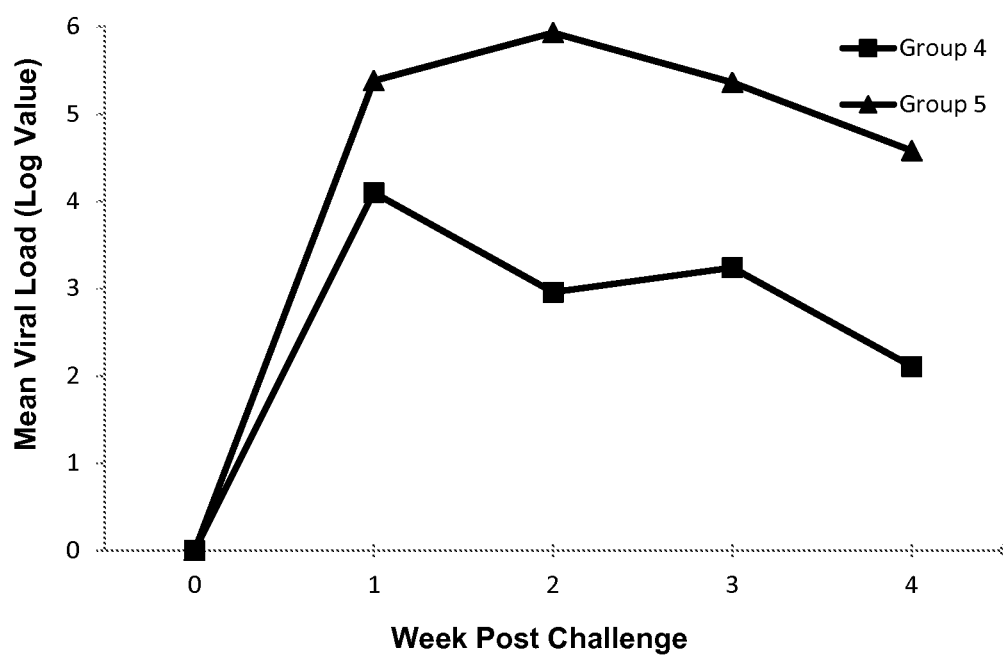
FIG. 7 is a graph showing geometric mean viral loads (Log) of Group 5 (placebo) and Group 4 (vaccinates) piglets post challenge with PCV2.

Serum samples collected on day 0, 7, 14, 21 and 28 post challenge were tested by qPCR as described in Example 4. The results were expressed as the number of copies per mL in the tested samples. The geometric mean viral loads (Log) of Group 5 (placebo control) and Group 4 (vaccinates) are shown in FIG. 7. All samples collected on day 0 were negative. All samples in Group 5 became positive at day 7 post challenge, while all but one sample from Group 4 was positive (data not shown). The average number of copies of the PCV2 genomic materials in 1 ml of the serum samples was 12,589, 912, 1737 and 125 in the vaccinated group (group 4) and in the placebo group (group 5) was 239, 883, 851,138, 229, 086 and 38,018 on day 7, 14, 21 and 28, respectively, post challenge. Accordingly, the reduction of virus load in the vaccinates (Group 4) as compared to group 5 (placebo) was 95% on day 7 and over 99% on day 14, 21, and 28 post challenge.

Statistical analysis revealed that viral loads in the vaccinated group (Group 4) were significantly lower than the placebo group (Group 5) on all sample dates after challenge. Viral load stayed high in the placebo group as evidenced by non-significant decreases in viral load on every sampling date, while the viral load significantly dropped from day 7 to day 14 and from day 21 to day 28 post challenge (data not shown). The qPCR and ELISA results show that a single 1 ml dose of the vaccine of Example 3 reduced viremia in the piglets caused by PCV2 infection.

Figure 8:
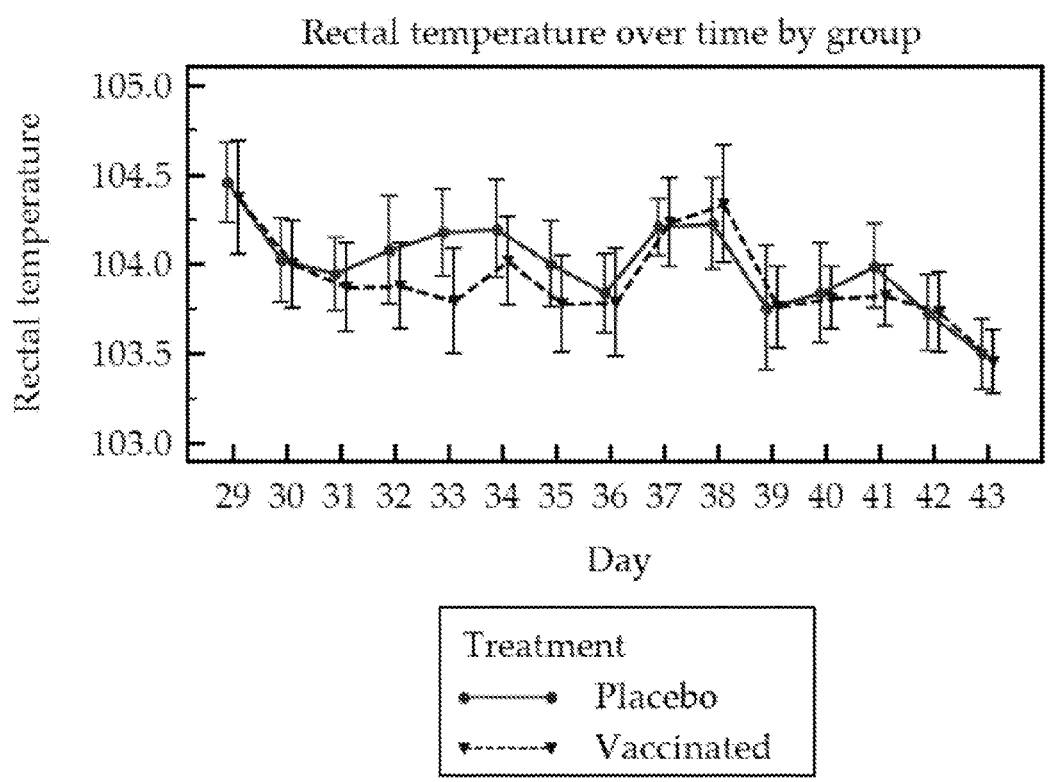
FIG. 8 is a graph showing the average rectal temperatures of Group 5 (placebo) and Group 4 (vaccinates) piglets post challenge with PCV2.

The piglets in Groups 4 and 5 were tested for temperature from day −2 to day 12 post challenge (day 29 to day 43 post vaccination). The average temperature in both Group 5 (placebo) and Group 4 (vaccinates) was high on the first day of temperature taking. There were no significant differences in temperature between Groups 4 and 5 on the days prior to the challenge and days of post challenge, except that on day 2 post challenge the temperature in the placebo group (Group 5) were significantly higher than that of the vaccinate group (Group 4), $p<0.05$ (data not shown). The average temperatures of Groups 4 and 5 are shown in FIG. 8.

Gross pathology and diagnosis were performed on day 28 post challenge as described in Example 4. The summary of histopathological and gross pathological diagnosis are shown in Table 12 (placebo) and Table 13 (vaccinates). Twelve of the 21 (57%) piglets in Group 5 (placebo) exhibited gross pathological signs consistent with the clinical signs of PCV2. Sixteen of the 21 piglets in the vaccinated group (Group 4) did not have gross lesions. The gross lesion reduction in the vaccinated group as compared with the placebo group was over 41%. This data, along with the significant temperature difference between the piglets in Group 5 (placebo) and Group 4 (vaccinates), shows that administration of a single 1 ml dose of the vaccine of Example 3 prevented virus colonization of lymphoid tissues, lymphoid depletion, and clinical signs caused by PCV2 infection in the piglets.

TABLE 12

| | Tonsil | | MLN | | ILN | | TBLN | | TOTALS | | Gross Pathology | |
| | IHC | LD | IHC | LD | IHC | LD | IHC | LD | IHC-total | LD-total | and Remarks | Diagnosis |
|---|---|---|---|---|---|---|---|---|---|---|---|---|
| 20  | 0 | 0 | 0 | 0 | 0 | 0 | 0 | 0 | 0 | 0 | See lymph node scores | Lymph node hypertrophy |
| 24  | 0 | 0 | 0 | 0 | 1 | 1 | 0 | 1 | 1 | 2 | See lymph node scores | Lymph node hypertrophy |
| 25  | 0 | 0 | 0 | 1 | 1 | 1 | 1 | 2 | 2 | 4 | No gross lesions | Normal |
| 26  | 0 | 0 | 0 | 0 | 1 | 1 | 0 | 0 | 1 | 1 | No gross lesions | Normal |
| 27  | 0 | 0 | 0 | 0 | 1 | 1 | 1 | 1 | 2 | 2 | No gross lesions | Normal |
| 31  | 0 | 0 | 0 | 0 | 1 | 0 | 0 | 0 | 1 | 0 | No gross lesions | Normal |
| 50  | 0 | 0 | 0 | 0 | 0 | 0 | 1 | 0 | 1 | 0 | No gross lesions | Normal |
| 77  | 0 | 0 | 0 | 1 | 0 | 0 | 1 | 1 | 1 | 2 | No gross lesions | Normal |
| 81  | 0 | 0 | 0 | 0 | 1 | 1 | 1 | 1 | 2 | 2 | Consolidation, see lymph node scores | minor pneumoniae and lymph node hypertrophy |
| 85  | 0 | 0 | 0 | 0 | 0 | 0 | 0 | 0 | 0 | 0 | No gross lesions | Normal |
| 87  | 0 | 0 | 0 | 0 | 0 | 0 | 0 | 0 | 0 | 0 | No gross lesions | Normal |
| 89  | 0 | 0 | 0 | 1 | 1 | 0 | 1 | 1 | 2 | 2 | No gross lesions | Normal |
| 95  | 0 | 0 | 0 | 0 | 0 | 0 | 0 | 0 | 0 | 0 | No gross lesions | Normal |
| 97  | 1 | 0 | 1 | 1 | 1 | 1 | 1 | 1 | 4 | 3 | See lymph node scores | Lymph node hypertrophy |
| 100 | 0 | 0 | 0 | 0 | 0 | 0 | 0 | 0 | 0 | 0 | No gross lesions | Normal |
| 107 | 0 | 0 | 0 | 0 | 0 | 0 | 0 | 0 | 0 | 0 | No gross lesions | Normal |
| 108 | 0 | 0 | 0 | 0 | 0 | 0 | 0 | 0 | 0 | 0 | See lymph node scores | Lymph node hypertrophy |
| 109 | 0 | 0 | 0 | 0 | 0 | 0 | 0 | 0 | 0 | 0 | No gross lesions | Normal |
| 110 | 0 | 0 | 0 | 0 | 0 | 0 | 0 | 0 | 0 | 0 | No gross lesions | Normal |
| 112 | 0 | 0 | 0 | 0 | 0 | 0 | 0 | 0 | 0 | 0 | No gross lesions | Normal |
| 113 | 1 | 1 | 1 | 2 | 1 | 2 | 2 | 1 | 5 | 6 | No gross lesions | Normal |

MLN: mesenteric lymph node
ILN: iliac lymph node
TBLN: tracheobronical lymph node
LD: lymphoid depletion

TABLE 13

| ID | Tonsil IHC | Tonsil LD | MLN IHC | MLN LD | ILN IHC | ILN LD | TBLN IHC | TBLN LD | TOTALS IHC-total | TOTALS LD-total | Gross Pathology and Remarks | Diagnosis |
|---|---|---|---|---|---|---|---|---|---|---|---|---|
| 19 | 2 | 2 | 1 | 2 | 0 | 2 | 1 | 2 | 4 | 8 | See lymph node scores | Lymph node hypertrophy |
| 21 | 2 | 2 | 2 | 2 | 2 | 3 | 2 | 3 | 8 | 10 | See lymph node scores | Lymph node hypertrophy |
| 23 | 2 | 1 | 1 | 1 | 1 | 1 | 1 | 0 | 5 | 3 | No gross lesions | Normal |
| 28 | 1 | 0 | 0 | 1 | 1 | 2 | 2 | 2 | 4 | 5 | Enteritis, see lymph node scores | Enteritis, lymph node hypertrophy |
| 29 | 2 | 2 | 2 | 2 | 2 | 1 | 2 | 1 | 8 | 6 | See lymph node scores | Mild lymph node hypertrophy present |
| 32 | 2 | 1 | 2 | 2 | 2 | 2 | 1 | 1 | 7 | 6 | See lymph node scores | Lymph node hypertrophy |
| 78 | 0 | 0 | 0 | 0 | 1 | 1 | 1 | 1 | 2 | 2 | No gross lesions | Normal |
| 79 | 1 | 1 | 0 | 0 | 1 | 1 | 1 | 0 | 3 | 2 | Mottled discoloration | minor pneumoniae |
| 80 | 1 | 1 | 1 | 1 | 1 | 0 | 1 | 0 | 4 | 2 | No gross lesions | Normal |
| 83 | 0 | 0 | 0 | 0 | 1 | 0 | 0 | 0 | 1 | 0 | See lymph node scores | Lymph node hypertrophy |
| 84 | 3 | 3 | 3 | 3 | 3 | 3 | 3 | 3 | 12 | 12 | Sever intralobular edema, consolidation, poor body condition | pneumoniae |
| 86 | 0 | 1 | 0 | 1 | 1 | 1 | 1 | 1 | 2 | 4 | Mottled discoloration, see lymph node scores | minor pneumoniae and lymph node hypertrophy |
| 88 | 1 | 0 | 1 | 1 | 1 | 1 | 1 | 0 | 4 | 2 | No gross lesions | Normal |
| 90 | 0 | 0 | 0 | 1 | 0 | 1 | 1 | 2 | 1 | 4 | No gross lesions | Normal |
| 91 | 0 | 0 | 0 | 0 | 1 | 1 | 1 | 1 | 2 | 2 | No gross lesions | Normal |
| 92 | 1 | 1 | 1 | 2 | 1 | 2 | 1 | 2 | 4 | 7 | See lymph node scores | Lymph node hypertrophy |
| 94 | 0 | 0 | 0 | 0 | 0 | 1 | 0 | 1 | 0 | 2 | No gross lesions | Normal |
| 96 | 0 | 0 | 0 | 0 | 1 | 1 | 1 | 0 | 2 | 1 | See lymph node scores | Lymph node hypertrophy |
| 99 | 0 | 0 | 0 | 0 | 1 | 1 | 1 | 0 | 2 | 1 | No gross lesions | Normal |
| 106 | 1 | 1 | 0 | 1 | 1 | 1 | 1 | 1 | 3 | 4 | See lymph node scores | Lymph node hypertrophy |
| 111 | 0 | 0 | 0 | 0 | 1 | 1 | 0 | 1 | 1 | 2 | No gross lesions | Normal |

Tonsil (t), mesenteric lymph node (MLN), sub-iliac lymph node (SLN) and tracheobronchial lymph node (TBLN) were collected from all piglets on the day of termination. The samples were examined and scored as described in Example 4. The results are summarized in Table 14. When comparing the IHC score between the two groups, highly significant differences were found in all the examined tissues; the p-values of MLN, SLN, T, TBLN were 0.011, 0.001, 0.0008 and 0.002, respectively. The individual piglet and tissue scores are shown in Tables 12 and 13.

TABLE 14

| Group | Score 0 | 1 | 2 | 3 | Median/Mean Score | P-value |
|---|---|---|---|---|---|---|
| MLN-IHC | | | | | | |
| 4 | 19 (91%) | 2 (9%) | 0 | 0 | 0/0.10 | |
| 5 | 12 (57%) | 5 (24%) | 3 (14%) | 1 (5%) | 0/0.67 | |
|   | 31 | 7 | 3 | 1 | | 0.011 |
| SLN-IHC | | | | | | |
| 4 | 12 (57%) | 9 (43%) | 0 | 0 | 0/0.43 | |
| 5 | 3 (14%) | 14 (67%) | 3 (14%) | 1 (5%) | 1/1.10 | |
|   | 15 | 23 | 3 | 1 | | 0.001 |
| T-IHC | | | | | | |
| 4 | 19 (91%) | 2 (9%) | 0 | 0 | 0/0.10 | |
| 5 | 9 (43%) | 6 (28%) | 5 (24%) | 1 (5%) | 1/0.91 | |
|   | 28 | 8 | 5 | 1 | | 0.0008 |
| TBLN-IHC | | | | | | |
| 4 | 13 (62%) | 7 (33%) | 1 (5%) | 0 | 0/0.43 | |
| 5 | 3 (14%) | 14 (67%) | 3 (14%) | 1 (5%) | 1/1.10 | |
|   | 16 | 21 | 4 | 1 | | 0.002 |

Figure 9:
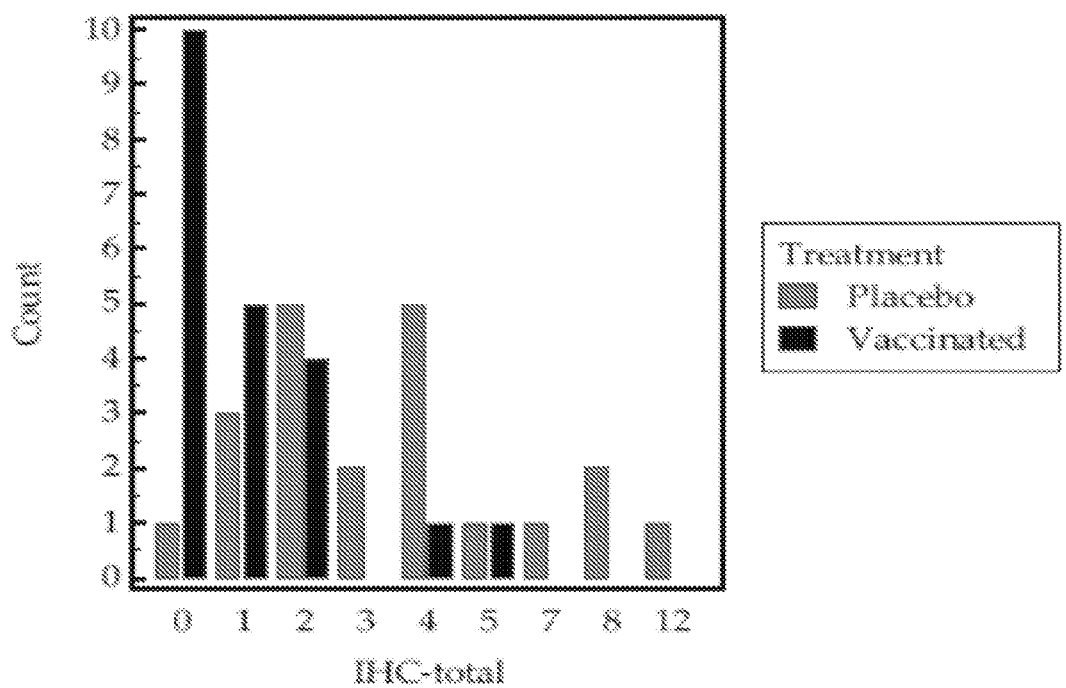
FIG. 9 is a graph showing the immunohistochemistry (IHC) score distribution upon PCV2 staining in lymph node tissue in Group 5 (placebo) and Group 4 (vaccinates) piglets post challenge with PCV2.

The overall scores between the vaccinated group and the placebo group are highly significant with a P value of 0.0002. The IHC score distribution of Group 4 and Group 5 are shown in FIG. 9. The results in Table 14 and FIG. 9 show that a single 1 ml dose of the vaccine of Example 3 reduced virus colonization of lymphoid tissues in the piglets caused by PCV2 infection.

Figure 10:
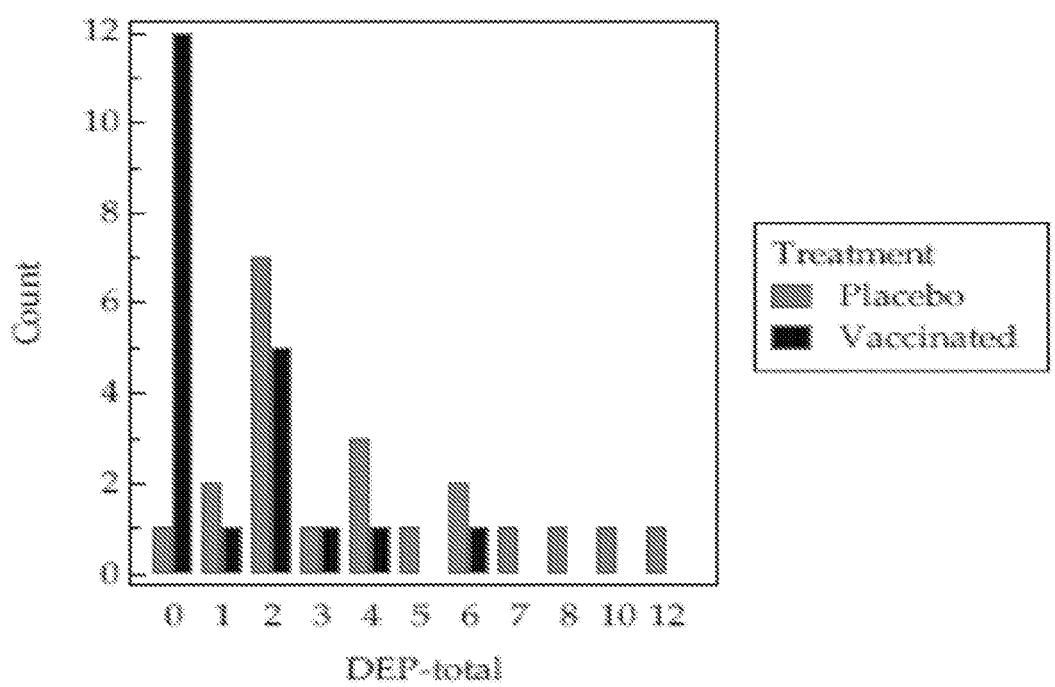
FIG. 10 is a graph showing lymphoid depletion in Group 5 (placebo) and Group 4 (vaccinates) piglets post challenge with PCV2.

When comparing the depletion scores in Groups 4 and 5, significant differences were found in all examined tissues, the p-values were 0.009, 0.0002, 0.0007 and 0.0267 for MLN, SLN, T, TBLN, respectively (data not shown). The score distribution is shown in FIG. 10. The overall depletion scores between the vaccinated and the placebo group show a highly significant difference with a P value of 0.0003. These results show that a single 1 ml dose of the vaccine of Example 3 reduced lymphoid depletion in the piglets caused by PCV2 infection.

Example 7

Efficacy of a Single Dose of Ready-To-Use Vaccine in Piglets Challenged With *M. hyopneumoniae*

A study of the efficacy of the ready-to-use vaccine of Example 3 in piglets against *M. hyopneumoniae* challenge was conducted. This study in conjunction with the PCV2 challenge study in Example 6 demonstrated that a single dose of the vaccine of Example 3 is efficacious against *M. hyopneumoniae* and PCV2 infections in piglets.

Forty-two CDCD piglets (mixed sex, age 12 days +/−1 day) were randomly divided into the following treatment groups as shown in Table 15. The piglets were *M. hyopneumoniae* antibody negative (S/P Ratio <0.4).

TABLE 15

| Group | Description | No. of Piglets | Treatment |
|---|---|---|---|
| 4 | Placebo control | 21 | Intramuscular (IM) injection of one 1 mL dose of PMT placebo |
| 3 | Vaccinates | 21 | Intramuscular (IM) injection of one 1 mL dose of PCV2-Mycoplasma *Hyopneumoniae* vaccine |

The piglets were vaccinated as shown in Table 15 and observed daily during the study for normal health. On day 33 post-vaccination, the piglets where challenged with *M. hyopneumoniae* lung inoculum (LI37) as described in Example 5. All piglets were challenged intratracheally with an 18 mL inoculum. Daily observation of the piglets showed all to have normal health throughout the duration of the study, except for one piglet in the vaccinates group, which was determined to have died of a twisted gut.

The piglets were terminated on day 37 post challenge and necropsied to score lung lesions. The lesion scores were expressed as the percentage of the lung surface area showing gross lesions typical of enzootic pneumonia as described in Example 5. The average lung lesion score in the vaccinated group (Group 3) was 4.34%. The average lung lesion score in the placebo group (Group 4) was 9.70%.

Mitigated Fraction analysis revealed the lung lesions scores of the piglets in Group 4 were significantly higher than that of the piglets in Group 3. A Mitigated Fraction of 0.4619 (95% CI: 0.1405, 0.7429) was estimated when the litter effect was not considered, while a Mitigated Fraction of 0.4419 (95% CI: 0.1471, 0.7000) was estimated when the litter effect was considered. Both demonstrated that the vaccine of Example 3 significantly reduced the lung lesion scores in the vaccinated piglets as compared with the piglets in the placebo group.

Lung tissue samples that contained lesions, as well as a portion of the apparently normal lung tissue adjacent to the lesions were analyzed by PCR for presence of *M. hyopneumoniae* in the sample as described in Example 5. One piglet in the vaccinated group (Group 3) was negative and 4 were suspect. The rest of piglets in Group 3 were positive. In Group 45, 19 out 21 (95%) piglets were PCR positive for *M. hyopneumoniae*, one was negative, and one was suspect. The lung lesion and PCR results show that a single 1 ml dose of the vaccine of Example 3 reduces lung lesions caused by *M. hyopneumoniae* infection.

While certain embodiments of the invention have been described, other embodiments may exist. While the specification includes a detailed description, the invention's scope is indicated by the following claims. Furthermore, while the specification has been described in language specific to structural features and/or methodological acts, the claims are not limited to the features or acts described above. Rather, the specific features and acts described above are disclosed as illustrative aspects and embodiments of the invention. Various other aspects, embodiments, modifications, and equivalents thereof which, after reading the description herein, may suggest themselves to one of ordinary skill in the art without departing from the spirit of the present invention or the scope of the claimed subject matter.

What is claimed is:

1. A method of reducing PCV2 infection in a pig, comprising administering to the pig a single dose of a multivalent vaccine comprising:
  at least 1 ELISA unit of recombinant PCV2 ORF2 capsid antigen, wherein the ELISA unit is determined by PCV2-Ag-51811 as the reference antigen;
  at least 60 micrograms of *Mycoplasma hyopneumoniae* antigen;
  a two component adjuvant system, the first component comprising a saponin adjuvant and the second component comprising an oil-in-water adjuvant or aluminum adjuvant; and
  a physiologically acceptable vehicle.

2. The method of claim 1, wherein the vaccine is administered to the pig within 1 to weeks of birth.

3. The method of claim 1, wherein the *Mycoplasma hyopneumoniae* antigen comprises inactivated or a lysate or sonicate of an inactivated or attenuated virulent *Mycoplasma hyopneumoniae*.

4. The method of claim 1, wherein the first component of the adjuvant system comprises a saponin adjuvant selected from the group consisting of *Quilaja* saponins, *Ginseng* saponins, *Panax notoginseng* saponins, *Platycodon grandiflorum* saponins, *Astragalus* saponins, *Achyranthes* saponins, and *Polygala* saponins.

5. The method of claim 1, wherein the saponin adjuvant is present at 50 microgram to 200 micrograms.

6. The method of claim 1, wherein the first component of the adjuvant system comprises Quil A saponin or a derivative thereof.

7. The method of claim 1, wherein the second component of the adjuvant system comprises 5% to 45% v/v of an oil-in-water adjuvant.

8. The method of claim 1, wherein the second component of the adjuvant system comprises an aluminum hydroxide gel.

9. The method of claim 1, wherein the multivalent vaccine further comprises a preservative.

10. The method of claim 1, wherein the single dose comprises a volume of 1 ml to 2 ml.

11. The method of claim 1, wherein the vaccine is administered orally, parenterally, intramuscularly, intranasally, or intravenously to the pig.

12. The method of claim 1, wherein the second component of the adjuvant system comprises 10% to 40% v/v of an oil-in-water adjuvant.

13. The method of claim 1, wherein the second component of the adjuvant system comprises 10% to 40% aluminum salt or gel comprising aluminum salt.

14. The method of claim 1, wherein the vaccine further comprises 0.005% to 0.01% thimerosal presentative.

15. A method of eliciting an immune response to PCV2 and *Mycoplasma hyopneumoniae* in a pig the method comprising:
  administering a single dose of a multivalent vaccine within 1 to weeks of birth, the vaccine comprising:
    at least 1 ELISA unit of recombinant PCV2 ORF2 capsid antigen, wherein the ELISA unit is determined by PCV2-Ag-51811 as the reference antigen;
    60-180 micrograms of *Mycoplasma hyopneumoniae* antigen;
    a two component adjuvant system, the first component comprising a saponin adjuvant and the second component comprising an oil-in-water adjuvant or aluminum adjuvant; and
    a physiologically acceptable vehicle.

16. The method of claim 1, wherein the method also induces an immune response to *Mycoplasma hyopneumoniae* infection in the pig.

* * * * *